US008512269B1

(12) United States Patent
Stano et al.

(10) Patent No.: US 8,512,269 B1
(45) Date of Patent: Aug. 20, 2013

(54) MOLDED ANKLE-FOOT ORTHOSES AND METHODS OF CONSTRUCTION

(76) Inventors: William Scott Stano, Boise, ID (US); Scott Davis Pixley, Boise, ID (US)

( * ) Notice: Subject to any disclaimer, the term of this patent is extended or adjusted under 35 U.S.C. 154(b) by 139 days.

(21) Appl. No.: 12/720,544

(22) Filed: Mar. 9, 2010

(51) Int. Cl.
*A61F 5/00* (2006.01)
(52) U.S. Cl.
USPC ............... 602/27; 602/5; 602/6; 602/65
(58) Field of Classification Search
USPC ..... 602/5, 23, 26–27, 20–21, 6, 65; 128/882; 36/54
See application file for complete search history.

(56) References Cited

U.S. PATENT DOCUMENTS

| | | | |
|---|---|---|---|
| 1,396,323 A | | 11/1921 | Dunne |
| 2,219,697 A | * | 10/1940 | Nickowitz ............... 36/44 |
| 2,897,610 A | * | 8/1959 | Campagna ............... 36/4 |
| 3,169,325 A | * | 2/1965 | Fesl ............... 36/117.1 |
| 3,641,688 A | | 2/1972 | von den Benken |
| 3,814,088 A | | 6/1974 | Raymond |
| 4,367,733 A | | 1/1983 | Stromgren |
| 4,517,968 A | | 5/1985 | Greene et al. |
| 4,869,001 A | | 9/1989 | Brown |
| 4,876,758 A | | 10/1989 | Rolloff et al. |
| 4,920,666 A | * | 5/1990 | Marega ............... 36/54 |
| 4,966,134 A | | 10/1990 | Brewer |
| 4,974,343 A | | 12/1990 | Davidson |
| 4,977,891 A | | 12/1990 | Grim |
| 4,981,132 A | | 1/1991 | Chong |
| 5,092,319 A | | 3/1992 | Grim |
| 5,187,815 A | * | 2/1993 | Stern et al. ............... 2/16 |
| 5,379,529 A | * | 1/1995 | Smith et al. ............... 36/54 |
| 5,381,610 A | * | 1/1995 | Hanson ............... 36/100 |
| 5,437,466 A | | 8/1995 | Meibock et al. |
| 5,472,414 A | | 12/1995 | Detty |
| 5,853,380 A | | 12/1998 | Miller |
| 5,893,222 A | | 4/1999 | Donnelly |
| 5,897,518 A | | 4/1999 | Shaw |
| 5,899,872 A | | 5/1999 | Gilmour |
| 5,943,793 A | * | 8/1999 | Clements ............... 36/89 |
| 5,944,679 A | | 8/1999 | DeToro |
| 6,024,712 A | | 2/2000 | Iglesias et al. |
| 6,056,713 A | | 5/2000 | Hayashi |
| 6,083,185 A | | 7/2000 | Lamont |
| 6,090,059 A | | 7/2000 | Wasserman et al. |
| 6,117,098 A | | 9/2000 | Weber et al. |
| 6,155,997 A | | 12/2000 | Castro |

(Continued)

OTHER PUBLICATIONS

Anonymous, AFO Instructions, Walkwell International Laboratories, 2007, http://walkwell-labs.com/afo.html (last visited Feb. 16, 2012).

(Continued)

*Primary Examiner* — Patricia Bianco
*Assistant Examiner* — Camtu Nguyen
(74) *Attorney, Agent, or Firm* — TraskBritt

(57) ABSTRACT

Disclosed is an ankle-foot orthosis that includes a boot and a pre-tibial shell. The boot includes an inner shell and outer shell between which are included padding and/or structural supports according to the needs of the patient to be treated. The pre-tibial shell likewise includes an interior layer and an exterior layer. Both the boot and the pre-tibial shell are custom molded to a casting made from an injured foot while taped in a non-weight-bearing position and corrected to a position of neutral pathology. Also disclosed is a method for constructing the disclosed ankle-foot orthosis.

20 Claims, 27 Drawing Sheets

(56) References Cited

U.S. PATENT DOCUMENTS

| | | | |
|---|---|---|---|
| 6,226,898 B1 | 5/2001 | Trimble et al. | |
| 6,230,423 B1 | 5/2001 | Donnelly | |
| 6,381,877 B2 | 5/2002 | Filice | |
| 6,394,971 B1 | 5/2002 | Slautterback et al. | |
| 6,398,750 B1 | 6/2002 | Quinn et al. | |
| 6,443,919 B1 * | 9/2002 | Castro | 602/27 |
| 6,478,762 B1 | 11/2002 | Varn | |
| 6,629,945 B1 | 10/2003 | Stromgren | |
| 6,652,474 B1 | 11/2003 | Quinn et al. | |
| D492,788 S | 7/2004 | Bird et al. | |
| 6,923,781 B2 | 8/2005 | Gardner et al. | |
| 6,931,766 B2 | 8/2005 | Greene | |
| 7,018,352 B2 | 3/2006 | Pressman et al. | |
| 7,128,725 B2 | 10/2006 | Rabe | |
| 7,335,177 B2 | 2/2008 | Reynolds et al. | |
| 7,468,047 B2 * | 12/2008 | Nieberding | 602/7 |
| 7,618,387 B2 | 11/2009 | Buethorn | |
| 7,871,389 B2 * | 1/2011 | Plake et al. | 602/23 |
| 2001/0004139 A1 | 6/2001 | Brown | |
| 2004/0034316 A1 | 2/2004 | Castro | |
| 2005/0096576 A1 | 5/2005 | Castro | |
| 2007/0199208 A1 | 8/2007 | Wilkenfeld | |
| 2007/0203441 A1 | 8/2007 | Castro | |
| 2010/0130900 A1 | 5/2010 | DeToro et al. | |

OTHER PUBLICATIONS

Anonymous, Walkwell Custom AFO, Walkwell International Laboratories, 2007, http://walkwell-labs.com/walkwell.html (last visited Mar. 19, 2010).

Anonymous, Casting Video, Walkwell International Laboratories, 2007, http://walkwell-labs.com/casting.html (last visited Feb. 16, 2012).

Anonymous, Casting Technique for Walkwell AFO, Excerpts (screen stills) from Video, 2003, Walkwell International Labs, available at http://walkwell-labs.com/casting.html (last visited Feb. 16, 2012).

Anonymous, Crow Walker Neuropathic AFO, Orthomerica Ther Global Orthotic Solution, 2011, http://www.orthomerica.com/custom/crow_walker.html (last visited Mar. 22, 2012).

Anonymous, Spectrum AFO System, Orthomerica, 2010, http://orthomerica.conn/spectrum/index.html (last visited Mar. 22, 2012).

Anonymous, Restoring Mobility Restores Life (excerpts), Arizona AFO, Inc., http://www.arizonaafo.com (last visited Mar. 29, 2012).

Anonymous, Orthomerica.com (excerpts), Orthomerica Products, Inc., 2003-2011, http://www.orthomerica.com (last visited Mar. 31, 2012) (part 1 of 9).

Anonymous, Orthomerica.com (excerpts), Orthomerica Products, Inc., 2003-2011, http://www.orthomerica.com (last visited Mar. 31, 2012) (part 2 of 9).

Anonymous, Orthomerica.com (excerpts), Orthomerica Products, Inc., 2003-2011, http://www.orthomerica.com (last visited Mar. 31, 2012) (part 3 of 9).

Anonymous, Orthomerica.com (excerpts), Orthomerica Products, Inc., 2003-2011, http://www.orthomerica.com (last visited Mar. 31, 2012) (part 4 of 9).

Anonymous, Orthomerica.com (excerpts), Orthomerica Products, Inc., 2003-2011, http://www.orthomerica.com (last visited Mar. 31, 2012) (part 5 of 9).

Anonymous, Orthomerica.com (excerpts), Orthomerica Products, Inc., 2003-2011, http://www.orthomerica.com (last visited Mar. 31, 2012) (part 6 of 9).

Anonymous, Orthomerica.com (excerpts), Orthomerica Products, Inc., 2003-2011, http://www.orthomerica.com (last visited Mar. 31, 2012) (part 7 of 9).

Anonymous, Orthomerica.com (excerpts), Orthomerica Products, Inc., 2003-2011, http://www.orthomerica.com (last visited Mar. 31, 2012) (part 8 of 9).

Anonymous, Orthomerica.com (excerpts), Orthomerica Products, Inc., 2003-2011, http://www.orthomerica.com (last visited Mar. 31, 2012) (part 9 of 9).

* cited by examiner

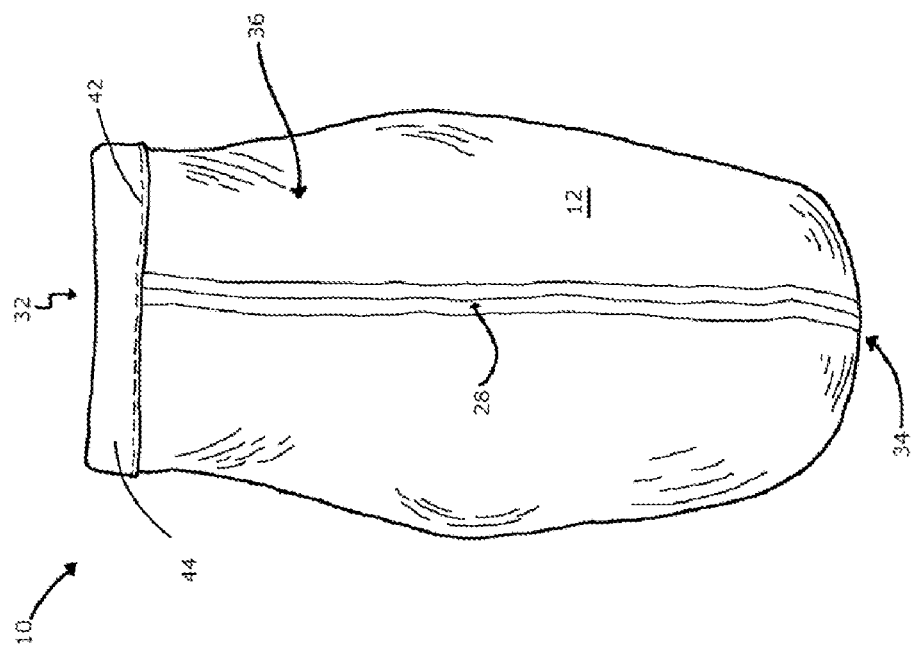
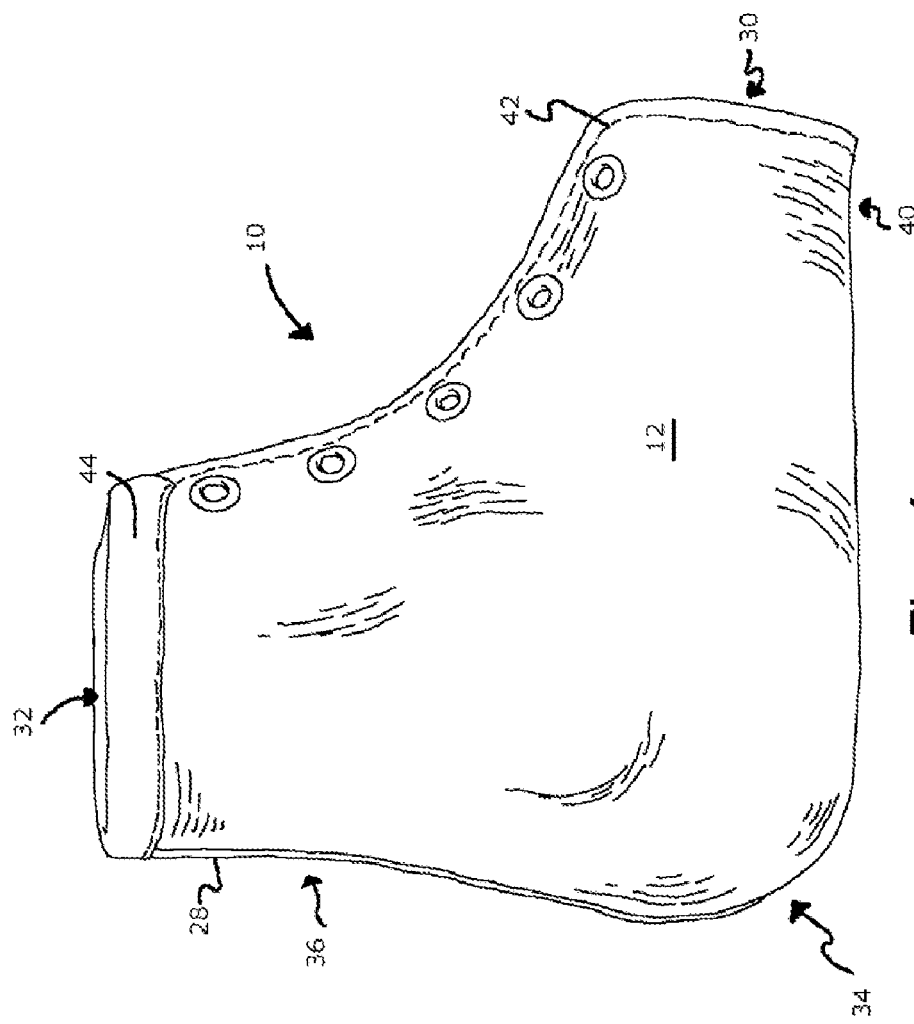

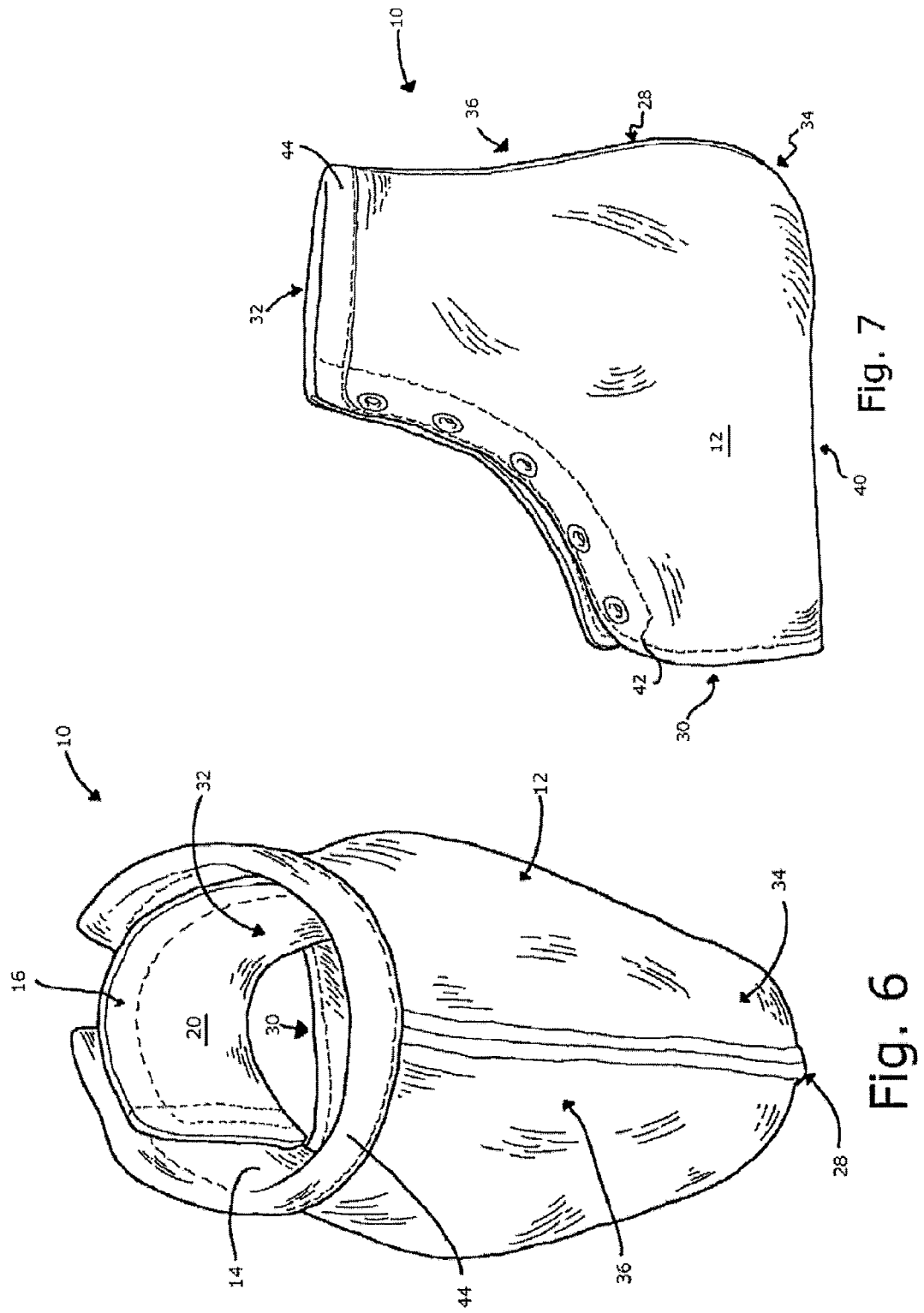

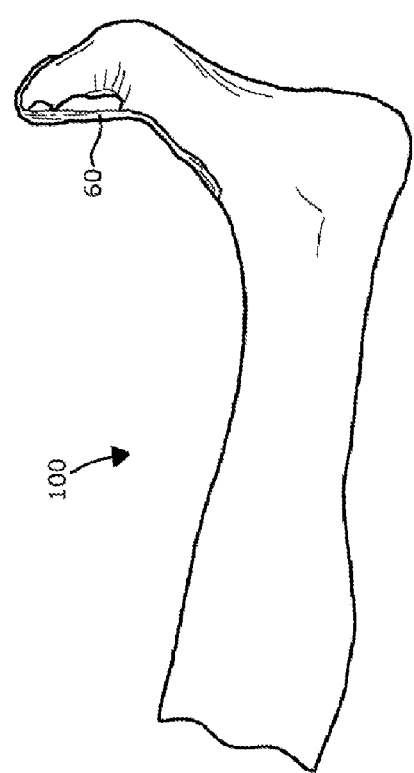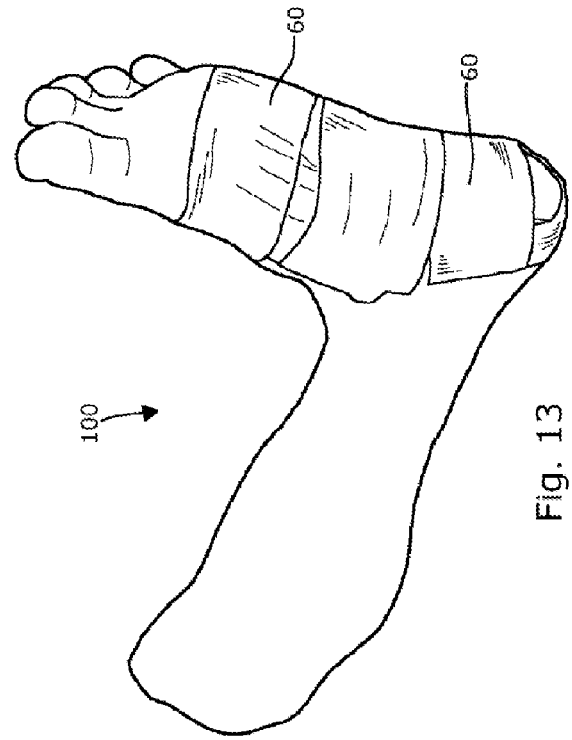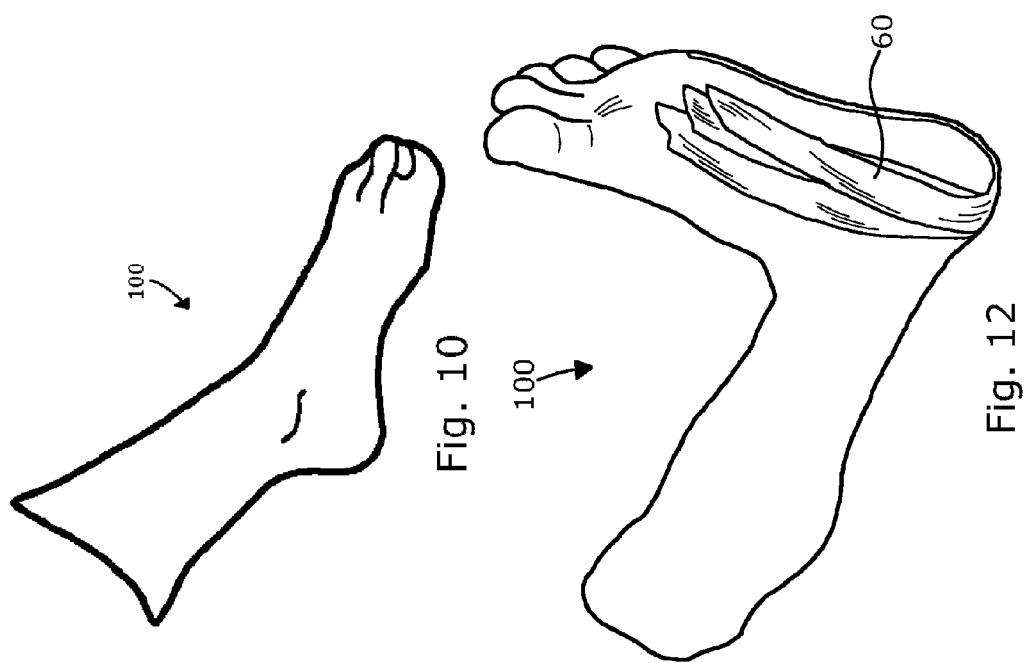

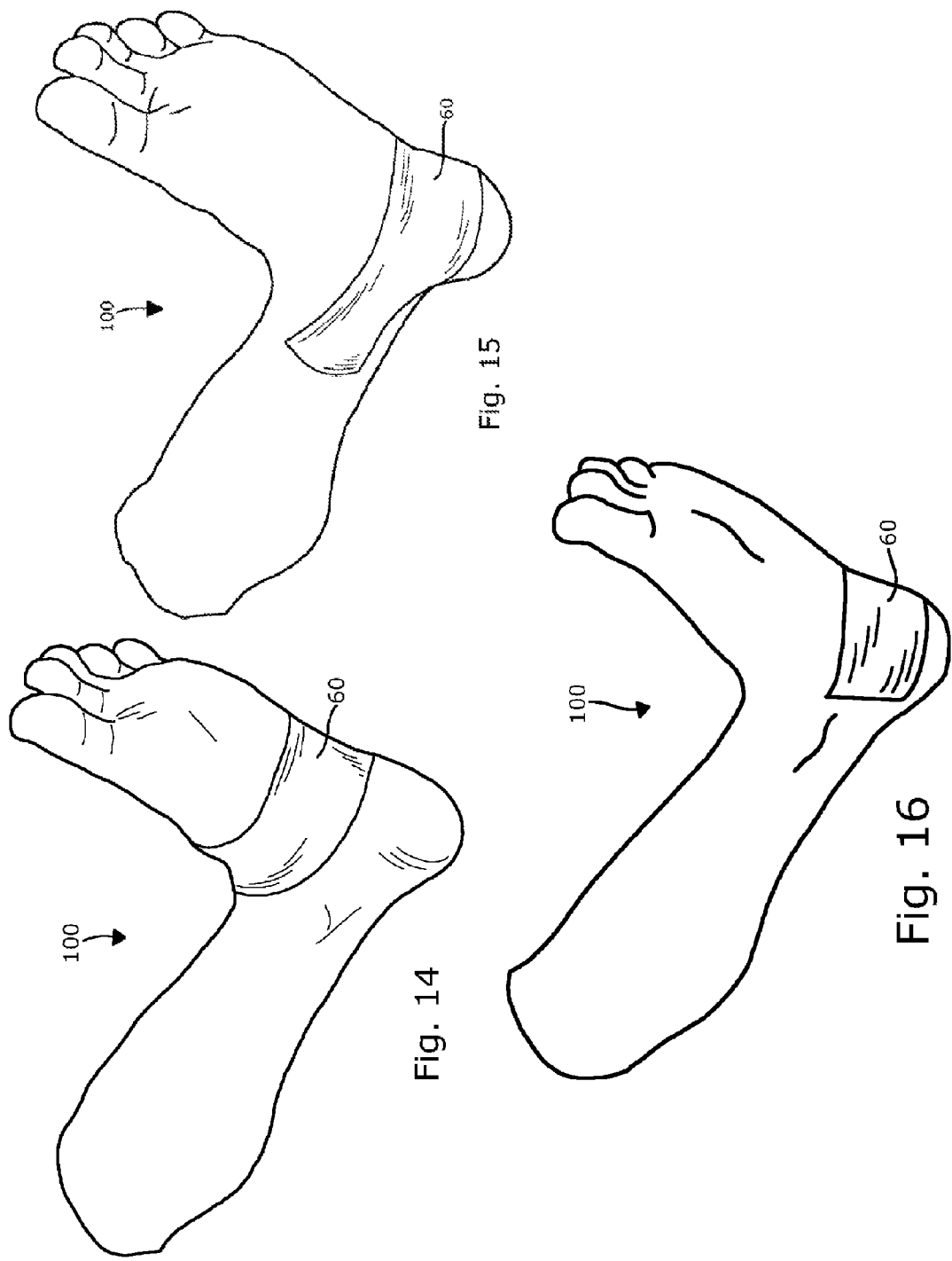

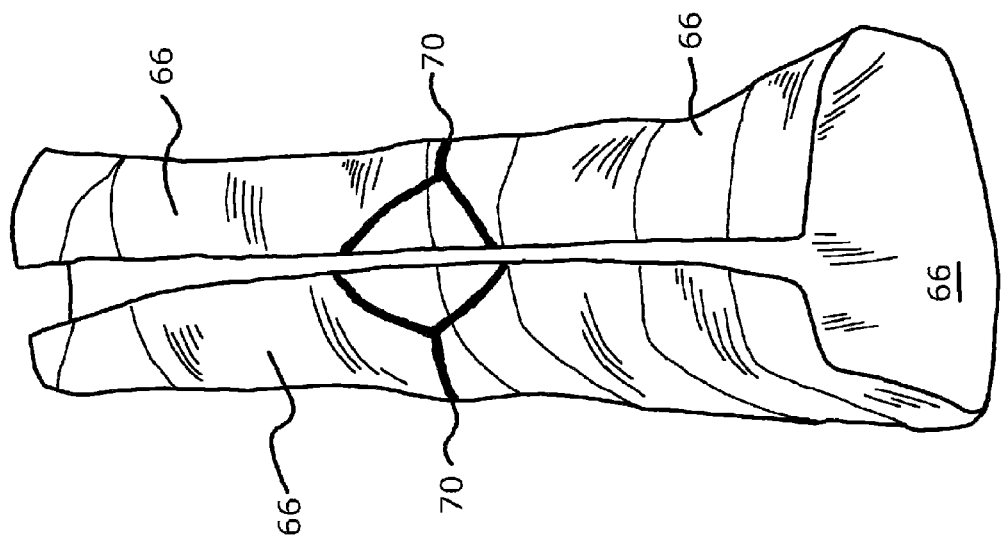
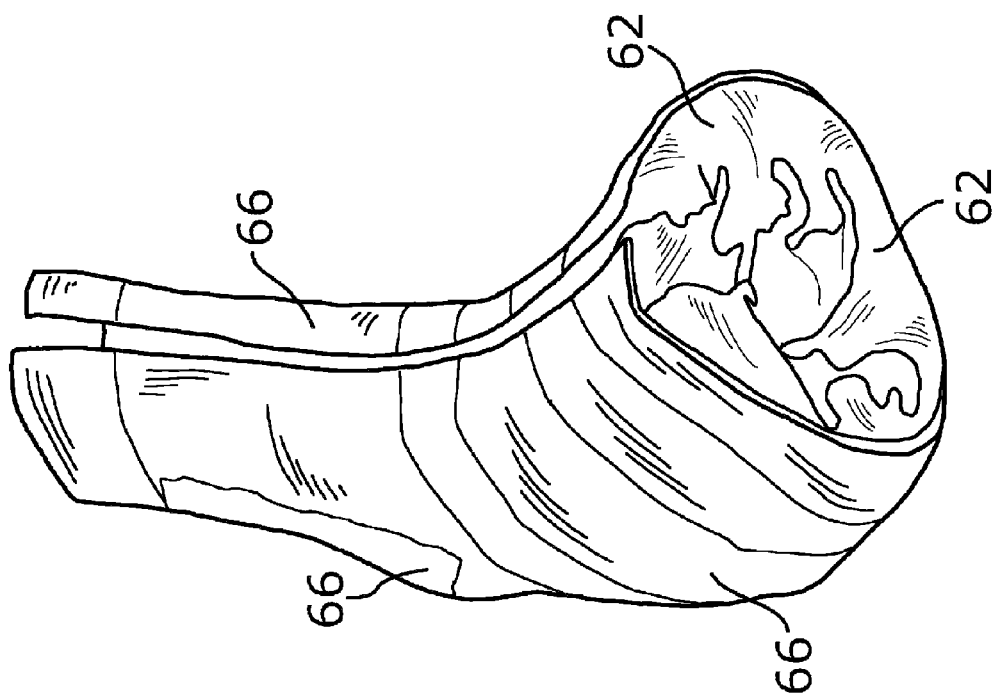
Fig. 26
Fig. 25

MOLDED ANKLE-FOOT ORTHOSES AND METHODS OF CONSTRUCTION

CROSS-REFERENCE TO RELATED APPLICATIONS

This application is related to the subject matter of U.S. patent application Ser. No. 13/436,210, filed Mar. 30, 2012, pending, which is a continuation-in-part of this application. This application is also related to the subject matter of U.S. patent application Ser. No. 13/454,955, filed Apr. 24, 2012, pending.

TECHNICAL FIELD

The invention generally relates to orthosis medical devices and, more specifically, to a molded ankle-foot orthosis and method for constructing a molded ankle-foot orthosis that is fully molded to an injured foot to be treated and that can be used for treating a variety of conditions without the need for surgery and while allowing non-injured areas of the foot to continue to function normally.

BACKGROUND OF THE INVENTION

The human foot takes the brunt of impact of every step experienced by an individual. When a person's foot becomes injured in some way, the foot must be somehow casted or braced in order to prevent movement of an injured area so as to encourage correction of the injury or to prevent movement of an area that has been surgically treated so that the benefits of the surgery will not be undone.

Casts, for example, can be applied to the foot. Traditional casts surround the injured patient's foot and so limit movement of the injured or surgically-treated area. However, traditional casts are fully rigid, preventing movement of the non-injured areas of the foot in addition to the injured or treated areas. Their heaviness and bulk also make mobility more difficult for the patient. Often the cast cannot be removed and reapplied.

Braces, on the other hand, are usually lighter than casts. This allows for more mobility by the patient. However, common braces are also usually not as rigid, which provides less protection to the injured area of the foot or the already-treated area of the foot. In braces that are partially rigid, the foot is prone to movement within the brace so that, again, the injured area of the foot or the already-treated area of the foot is not always as protected or immobilized as it should be. Further, traditional braces are not of a customized shape, but are more of a one-size-fits-all. As such, they are not well suited for use with patients with any but the average shape of foot. Some traditional braces include hinges to allow the foot to move up and down, but not side to side. These braces, while allowing some movement of the patient's foot, do not accommodate the natural tri-planar movement of the foot.

SUMMARY OF THE INVENTION

The present molded ankle-foot orthosis provides for a non-bulky, light, custom-molded orthosis that can be used to treat any of a large number of pathologies without surgery or to protect feet that have already been treated through surgery. For example, it can be used to treat ambulatory patients who have weakness or deformity in the foot and/or ankle, who require stabilization in the foot and ankle, and who have the potential to benefit from better function of the otherwise-injured foot. It includes a boot having an outer shell and a seamless inner shell. Between the inner shell and outer shell are located, at select points, padding and/or structural supports. Attached to the boot is a pre-tibial shell that includes an interior layer and an exterior layer. Also between the interior and exterior layers of the pre-tibial shell are located, at select points, padding and/or structural supports. Both the boot and pre-tibial shell are custom molded to an injured foot that is taped before casting in a non-weight-bearing position.

Casting of the foot in the non-weight-bearing position allows the caster to correct the position of the foot to reduce deformities in the untreated foot in each of the sagital, transverse, and frontal planes before and while the foot is being casted. Accordingly, the negative cast created is not a cast of the foot's deformed or injured position, but of the foot's healthy, neutral foot position. Further, this non-weight-bearing casting position allows the natural arch of the foot to be casted, as opposed to traditional casting methods that result in molds or casts that must be adjusted to allow for the arch of the patient's foot. Position corrections are made during taping to a first corrected position as well as during casting to a second corrected position and then a third corrected position. Position corrections can also be made to the casted negative cast and to the mold made therefrom. The position-corrected mold is then used to stretch mold the inner shell of the boot, the outer shell of the boot, the interior layer of the pre-tibial shell, and the exterior layer of the pre-tibial shell. Thus, the custom-molded ankle-foot orthosis is formed so as to treat the injured foot, not accommodate the positional inaccuracies of the injured foot.

The ankle-foot orthosis is initially essentially fully rigid, and thus provides full protection over the bulk of the foot. Over time, through use, the ankle-foot orthosis becomes more flexible, except in areas in which rigid structural supports have been included between the inner and outer layers of the ankle-foot orthosis. Accordingly, as the patient progresses through treatment, the healthy areas of the foot are able to move as they normally would, while the injured areas or the areas needing protection remain protected and immobilized. Pressure points on the foot are not overly pressured, and atrophy is avoided.

Further, because the ankle-foot orthosis allows for some movement of the foot, particularly as the orthosis becomes more flexible over time, the ankle-foot orthosis is well suited for patients leading a dynamic lifestyle. It allows for a more normal gait to be maintained, rather than a stepping or flat-footed gait. It allows for relatively easy ambulation on inclines as well. In particular, a patient could wear an ankle-foot orthosis on each foot without having to use crutches to walk.

Still further, as the ankle-foot orthosis is worn over time and becomes more flexible, at least where not impeded by structural supports between the inner shell and outer shell or between the interior layer and the exterior layer of the pre-tibial shell, an intrinsic tri-planar hinge is essentially created, allowing the patient to move in each of the natural three planes of movement, including dorsiflexion, plantarflexion, and subtalar flexion, unless otherwise impeded by structural supports. Thus, the flexibility of the orthosis increases to keep pace with the treatment of the pathology.

The natural semi-flexibility of the leather used for the boot and pre-tibial shell allows the ankle-foot orthosis to accommodate natural changes in the patient's foot. For example, fluid in the foot changes throughout the day as a foot experiences swelling and/or reduction in swelling. The flexibility of this ankle-foot orthosis as well as the adjustability of the tightness of the closure device allows the patient to wear the orthosis throughout the day and over the course of days, weeks, or longer, as the foot undergoes these minor changes without serious adjustments needing to be made. It can also be worn at night. The leather composition further allows for more breathability than a plastic encasement would allow and reduces the likelihood of skin irritations.

Importantly, both the inner shell and the outer shell of the boot and the interior layer and exterior layer of the pre-tibial shell are essentially rigid, at least initially. As such, even the inner shell of the boot and the interior layer of the pre-tibial shell perform a treating function on the injured foot wearing the ankle-foot orthosis in that they restore the injured foot to a normal anatomic position. That is, the inner shell and the interior layer of the pre-tibial shell are not just liners or cushions, but have a form configured to hold the injured foot. Even without the outer shell and exterior layer of the pre-tibial shell in place, therefore, the inner shell, in conjunction with the interior layer of the pre-tibial shell, exhibit some circumferential control on the injured foot.

Also, notably, the pre-tibial shell serves a treatment function in the ankle-foot orthosis. It does more than simply cover the tibial area of the foot. The custom-molded pre-tibial shell provides sagital plane stability of the tibia over the talus to prevent abnormal motion of the foot, motion that would be common to many foot deformities. The restrictiveness resulting from the pre-tibial shell is affected by the selection of leather used to form the interior layer and exterior layer of the pre-tibial shell and by use, type selected, and thickness of structural supports included between the interior and exterior layers of the pre-tibial shell.

Further, because the ankle-foot orthosis is custom molded essentially to the shape of the entire foot, including the tibial area, except for the toes, the foot will be generally cradled by the entire ankle-foot orthosis, which therefore provides circumferential control of the injured foot. Thus, the ankle-foot orthosis can treat issues on the rear of the foot, on the top of the foot, on the inner portion of the foot, on the outer portion of the foot, and/or on the bottom of the foot. The circumferential cradling further holds the foot in a neutral position, which provides for better knee and hip stability of the patient during use. The circumferential control also allows for control of the foot and ankle in all three natural planes. The circumferential cradling results in the dissipation of the force that would otherwise be applied to more particularized areas of the foot's structure and avoids deformation forces that exceed seven pounds per square inch at pressure points. This is important for patients like diabetics having impaired sensation and for osteopenic patients having brittle, aged bones. In any regard, the orthosis promotes a position needed to perform daily tasks and keeps the muscles of the foot in physiological tension.

The ankle-foot orthosis is constructed based on what surgery would normally seek to accomplish. For example, with a patient having a selective fault at a specific anatomic area, construction of the present ankle-foot orthosis is keyed to that area and structural supports are included at that area so as to immobilize the injured area, just as surgery would focus on that area by fusing the joint at that location. Accordingly, only the portion of the ankle-foot orthosis that covers the joint to be protected would remain rigid during use of the orthosis. This allows the non-injured joints to continue with normal mobility. Known orthotics are rigid, and permanently so, in more areas than just the injured joint, thus immobilizing even healthy joints. This has an effect on the foot more akin to a surgeon fusing every joint of the foot, rather than just an injured joint. The construction method of this ankle-foot orthosis, however, reduces or eliminates the risk of atrophy because the ankle-foot orthosis restricts movement in only select areas of the patient's foot, i.e., areas where structural supports are included between the outer and inner shells of the boot of the orthosis and between the exterior and interior layers of the pre-tibial shell. Thus, again, healthy joints are allowed to function while only the diseased, injured, or otherwise functionally-deficient areas are subjected to steady prohibition of movement due to the structural supports.

Because the orthosis is custom molded, it can be used to treat a large range of the patient population, including patients who have muscle function and those suffering from pathologies that are only beginning to present, as opposed to only those suffering from end-stage pathologies. Thus, it useful to treat any of a large number of pathologies. Particularly, it can be used to address issues with muscles, joints, ligaments, tendons, soft tissue, nerves, and/or bone. It can be used to treat patients having neurological, circulatory, or orthopedic conditions for which a custom-molded orthosis reduces the chance of tissue injury. It is expected to be particularly beneficial in treating conditions that are permanent or of extended durations, such as those lasting more than six months. Though the ankle-foot orthosis can be used to treat pathologies without requiring surgery, it is also helpful to those patients who have already had surgery and are recuperating and to those patients who are healing after a fracture or who have had fractures heal in an irregular way such that they are lacking the normal anatomical integrity or anthropometric proportion.

As a first example, an embodiment of the ankle-foot orthosis is used to treat tarsal tunnel syndrome. A patient suffering from tarsal tunnel syndrome has a posterior tibial nerve coming out of the ankle and riding under the flexor ligament on the inside of the ankle. Abnormal external motion of the foot builds up pressure under the ligament, leading to a thickening of the ligament and entrapment of the nerve, which causes shooting nerve pain in the foot. Surgery has only limited success in treating this condition. Traditional orthotics, i.e., those created using a weight-bearing casting technique or other casting technique in which the cast includes the deformity of the foot, do not hold the foot in a neutral position. As such, these traditional orthotics further aggravate the nerve. However, use of the present ankle-foot orthosis positions the injured foot into a neutral position, thereby dissipating the pressure on the ligament and resolving the symptoms without surgery.

As a second example, an embodiment of the ankle-foot orthosis is used to treat distal tarsal tunnel syndrome. This condition is a more recent understanding and was commonly thought of as a heel spur or plantar fasciitis that would not heal. A patient suffering from distal tarsal tunnel syndrome exhibits pain for more than three to six months where the pain is a result of nerves of the posterior tibia nerve that branch as they come out of the foot and into the arch and are pinched during repeat thickening of chronic plantar fasciitis. This condition is traditionally addressed through surgery. However, the present ankle-foot orthosis holds the foot in a neutral position and the circumferential nature of this orthosis (i.e., that the foot is encased in a fully-molded orthosis) leads to decreased symptoms. This limits the need for surgery and saves the patient the expense of that traditional treatment.

As a third example, an embodiment of the ankle-foot orthosis is used to treat pes planus, which is characterized by a flat foot. This is due to medial (inner arch) collapse of the posterial tibial tendon, which takes its origin in the leg, as well as the spring ligament that holds the talus to the navicular bone on the underside of the joint. As a result, the foot turns outward and leads to knee and arch pain. An embodiment of the present ankle-foot orthosis that includes structural support between the inner shell and outer shell of the boot at the area of the navicular joint holds the foot in a corrected position and supplements the function of the posterior tibial tendon, which is weakened and has lost its functional physiologic tension. Holding the foot in a corrected position, more specifically, prevents the fibers of the posterior tibial tendon from tearing or sliding in a longitudinal fashion, which would lead to different grades of deformity.

As a fourth example, an embodiment of the ankle-foot orthosis is used to treat pes cavus, a condition characterized by an unstable, high-arched foot. This is classically found in ankle sprains, and this condition is traditionally addressed only by surgery, either to repair the ligament complex or to change the bone structure to lower the arch height. In an embodiment of the ankle-foot orthosis that includes a wedge either inside the orthosis or between the inner and outer shells of the boot and in which structural support is provided under the calcaneal cuboid joint, the injured foot is held in a position in which the heel is pitched into valgus. Again, because the ankle-foot orthosis provides circumferential control of the foot, it provides tri-planar control, which, in this case, helps to prevent recurrent sprains and ankle fractures.

As a fifth example, an embodiment of the ankle-foot orthosis is used to address arthritic joins. An arthritic joint has worn cartilage, leading to bone-on-bone rubbing, which leads to pain at the joint. Traditional treatment of this condition is surgery to replace the joint or to fuse the joint. Use of the present ankle-foot orthosis allows the motion of the foot to be limited, particularly at joints where structural supports are included, so as to spare the remaining cartilage. Thus, the motion of the joints is limited without having to fuse the joint.

The foregoing examples are not exhaustive. Other pathologies may be treated with the present ankle-foot orthosis, including pathologies such as instable joints, Achilles Tendinosis, peroneal tendinosis, Lisfranc, ankle pain, knee instability, HAV (Hallux aducto valgus), Charcot-Marie tooth disease, and Equinus. Still other features and advantages of the claimed ankle-foot orthosis and method for constructing the orthosis will become readily apparent to those skilled in this art from the following detailed description describing preferred embodiments of the orthosis and method, simply by way of illustration of the best mode contemplated by carrying out the orthosis and method. As will be realized, the ankle-foot orthosis and method are capable of modification in various obvious respects, all without departing from the invention. Accordingly, the drawings and description of the preferred embodiments are to be regarded as illustrative in nature, and not as restrictive in nature.

The purpose of the foregoing summary is to enable the public, and especially the scientists, engineers, and practitioners in the art who are not familiar with patent or legal terms or phraseology, to determine quickly from a cursory inspection, the nature and essence of the technical disclosure of the application. The summary is neither intended to define the invention of the application, which is measured by the claims, nor is it intended to be limiting as to the scope of the invention in any way.

BRIEF DESCRIPTION OF THE DRAWINGS

FIG. 4 is a right side elevation view of an ankle-foot orthosis according to the first embodiment.
FIG. 5 is a back side elevation view of an ankle-foot orthosis according to the first embodiment.
FIG. 6 is a top and back side perspective view of an ankle-foot orthosis according to the first embodiment.
FIG. 7 is a left side elevation view of an ankle-foot orthosis according to the first embodiment.
FIG. 10 is a top and right side perspective view of an injured foot for which an ankle-foot orthosis is to be made.
FIG. 11 is a right side elevation view of an injured foot taped and positioned in a first corrected position with a first taping configuration during the construction of an ankle-foot orthosis.
FIG. 12 is a front and right side perspective view of an injured foot partially taped during positioning of the foot into a first corrected position with a second taping configuration during the construction of an ankle-foot orthosis.
FIG. 13 is a front and right side perspective view following that shown in FIG. 12 in which the injured foot is taped and positioned in a first corrected position with a second taping configuration during the construction of an ankle-foot orthosis.
FIG. 14 is a front and right side perspective view of an injured foot taped and positioned in a first corrected position with a third taping configuration during the construction of an ankle-foot orthosis.
FIG. 15 is a front and right side perspective view of an injured foot taped and positioned in a first corrected position with a fourth taping configuration during the construction of an ankle-foot orthosis.
FIG. 16 is a front and right side perspective view of an injured foot taped and positioned in a first corrected position with a fifth taping configuration during the construction of an ankle-foot orthosis.

FIG. 25 is a front perspective view following that shown in FIG. 24 after removing the negative cast and cut stockinet sock from the injured foot during the construction of an ankle-foot orthosis.

FIG. 26 is a front perspective view following that shown in FIG. 25 after removing the stockinet sock from the negative cast during the construction of an ankle-foot orthosis.

DETAILED DESCRIPTION

Figure 1:
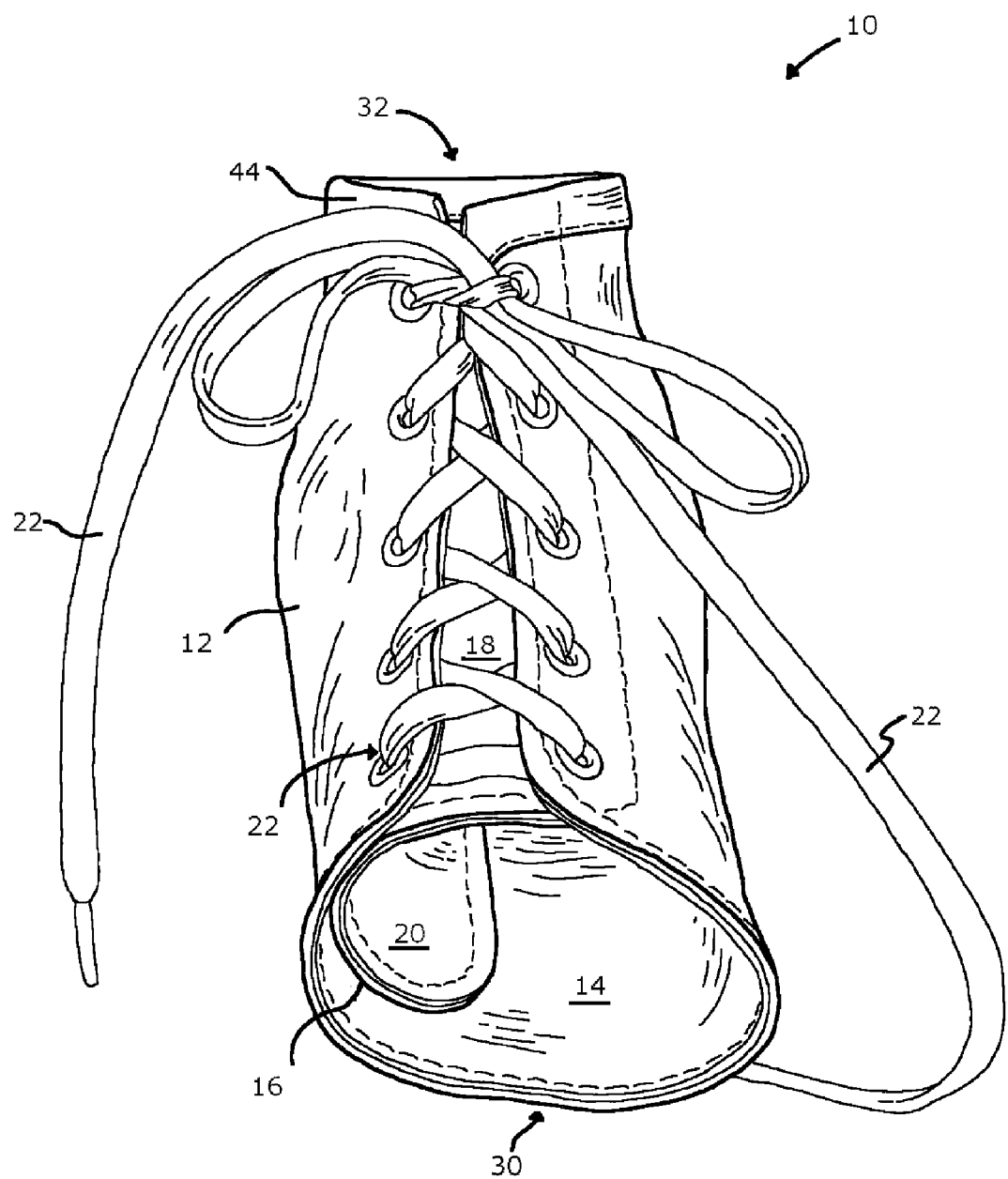
FIG. 1 is a front perspective view of an ankle-foot orthosis according to a first embodiment.

While the ankle-foot orthosis and method of construction are susceptible of various modifications and alternative constructions, certain illustrated embodiments thereof have been shown in the drawings and will be described below in detail. It should be understood, however, that there is no intention to limit the ankle-foot orthosis and method to the specific forms disclosed, but, on the contrary, the invention is to cover all modifications, alternative constructions, and equivalents falling within the spirit and scope of the invention as defined in the claims.

As shown in the figures, for purpose of illustration, the ankle-foot orthosis is embodied in a fully custom-molded combination of a singular inner shell and an outer shell to which is attached a molded pre-tibial shell, which also has an interior layer and an exterior layer, like the singular inner shell and the outer shell. Structural supports, padding, and/or wedges are included between the inner shell and outer shell where necessary to treat any of a number of pathologies exhibited by a patient's injured foot. The ankle-foot orthosis is constructed by a method that allows for adjustments from the shape of the injured foot at a number of points in the construction process, including at initial casting, at creation of a negative cast, and at stretch and heat molding of leather of the inner shell and the outer shell of a boot and the interior layer and exterior layer of a pre-tibial shell. The method of construction further allows for selection of an amount and location for thickness of supports and padding. Stiffness or flexibility of the leather of the inner shell and outer shell of the boot and the interior and exterior layer of the pre-tibial shell is also selective during the construction method.

In the following description and in the figures, like elements are identified with like reference numerals. The use of "e.g.," "etc.," and "or" indicates non-exclusive alternatives without limitation unless otherwise noted. The use of "including" means "including, but not limited to," unless otherwise noted.

Figure 46:
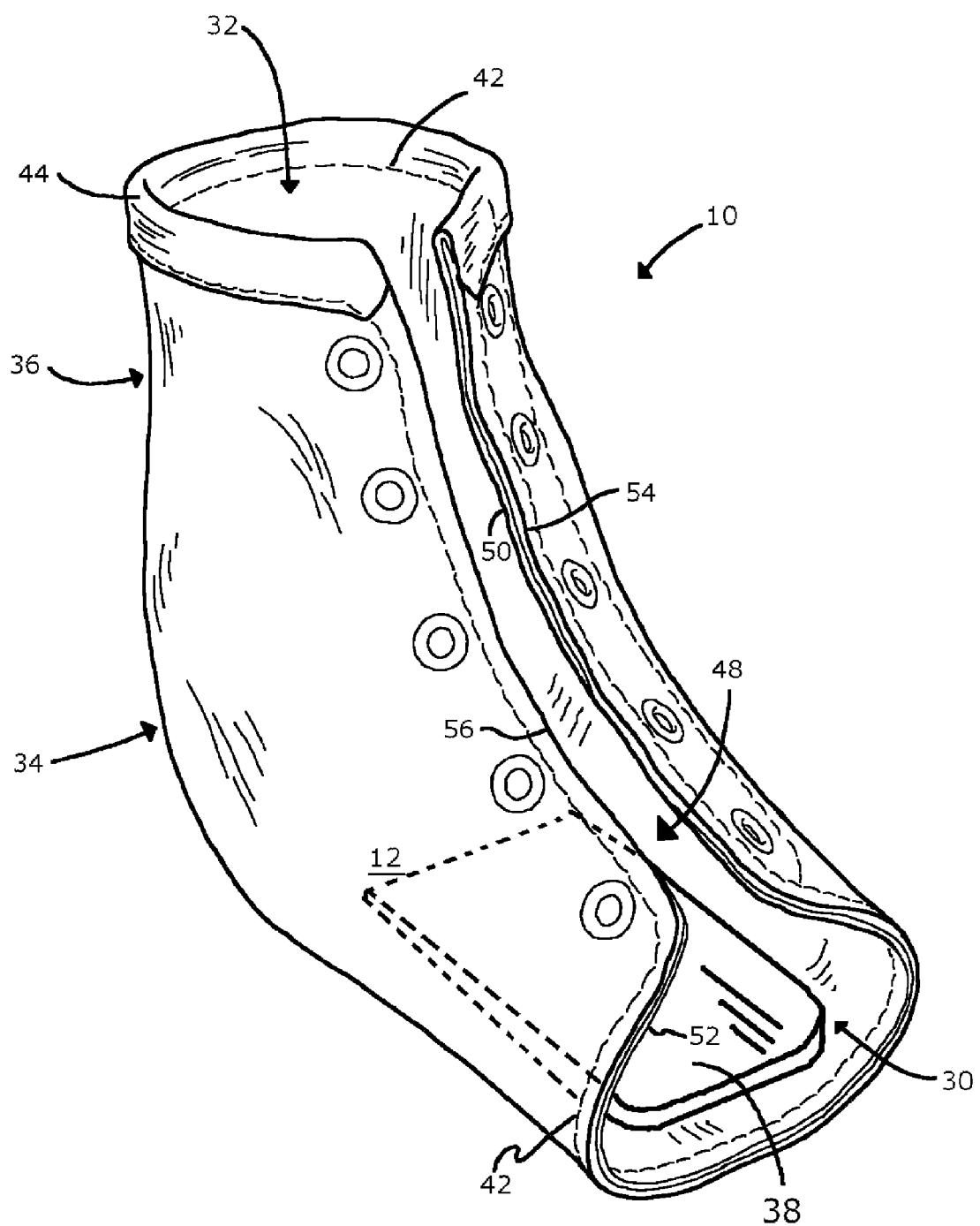
FIG. 46 is a front and right side perspective view of that shown in FIG. 45 with a wedge included therein during the construction of an ankle-foot orthosis.

A first embodiment of the ankle-foot orthosis 10 is shown in FIG. 1 and FIGS. 3 through 9. A second embodiment of the ankle-foot orthosis 10 is shown in FIG. 2. The ankle-foot orthosis 10 includes an inner shell 14, preferably a singular and seamless inner shell 14, that is made from leather that has been custom molded to a casting that has been made of a patient's injured foot 100 (FIG. 10) while the injured foot 100 is in a non-weight-bearing position and corrected to a position of neutral pathology. The inner shell 14 defines a left inner edge 50 and right inner edge 52 (FIG. 46).

The ankle-foot orthosis 10 further includes an outer shell 12 that largely surrounds the inner shell 14. The outer shell 12 is preferably made from leather that has also been custom molded, for the most part, to the inner shell 14. A single seam 28 is found in the rear of the outer shell 12. The outer shell 12 defines a left outer edge 54 and a right outer edge 56. As shown in FIG. 46, the left outer edge 54 aligns with the left inner edge 50 of the inner shell 14, and the right outer edge 56 aligns with the right inner edge 52 of the inner shell 14. The inner shell 14 and the outer shell 12 thereby define a pre-tibial slit 48 bordered by the left inner edge 50 and left outer edge 54 on one side and bordered by the right inner edge 52 and right outer edge 56 on the other side.

The ankle-foot orthosis 10 also includes a pre-tibial shell 16, which includes an interior layer 20 and an exterior layer 18. The interior layer 20 is preferably made from leather that has been custom molded to the casting made of the patient's injured foot 100 while the injured foot 100 is in a non-weight-bearing position and corrected to a position of neutral pathology. Preferably, the interior layer 20 is made from the same leather from which the inner shell 14 is made. The exterior layer 18 of the pre-tibial shell 16 is also preferably made from leather that has been custom molded, at least in part, to the interior layer 20. Preferably, the exterior layer 18 is made from the same leather from which the outer shell 12 is made. The pre-tibial shell 16 is fixedly attached to the inner shell 14 and is configured to span the pre-tibial slit 48. As such, when worn by the injured foot 100, the ankle-foot orthosis 10 surrounds the injured foot 100, providing circumferential support, except at the toes and at the shin and calf areas.

It is preferred that the leather used to make the inner shell 14, outer shell 12, and pre-tibial shell 16 is vegetable-tanned leather, not chromium-tanned leather. Therefore, the construction process is more environmentally friendly in not using the potentially-hazardous and polluting chromium chemical. Also, vegetable-tanned leather accommodates a leather-molded shape that is relatively rigid and will hold its shape, at least before substantial wear. It is further preferred that the leather not be pre-stretched prior to the construction process and not be subjected to chemical dyes. Thus, the ankle-foot orthosis 10 is dermatologically safe and can be used by patients having allergies to chemical dyes. The non-prestretched leather allows the leather to be spot stretched for select thinning of the leather in selected areas. More particularly, the leather used to make the inner shell 14 and interior layer 20 of the pre-tibial shell 16 is preferably orthopedic grade, vegetable-tanned leather that is not pre-stretched, not chemically dyed, and of a weight between one and three ounces per square foot. Further, the leather used to make the outer shell 12 and exterior layer 18 of the pre-tibial shell 16 is preferably vegetable-tanned leather that is not pre-stretched, not chemically dyed, and of a weight between three and six ounces per square foot. The thickness of the leather used for the inner shell 14 and interior layer 20 of the pre-tibial shell 16 and the leather used for the outer shell 12 and exterior layer 18 of the pre-tibial shell 16 is preferably chosen in consideration of the patient's pathology, neuropathic status, age, weight, activity level, or other patient-specific characteristics.

The inner shell 14 and outer shell 12 define a front opening 30, configured to allow the toe area of the injured foot 100 to be positioned outside of the ankle-foot orthosis 10. The inner shell 14 and outer shell 12 also define a top opening 32 that is preferably bordered by a top cuff 44 formed by a top portion of the inner shell 14 overlapping a top portion of the outer shell 12 in a region proximate to the top opening 32. The top opening 32 is configured to allow the shin and calf of the patient wearing the ankle-foot orthosis 10 to extend out of the ankle-foot orthosis 10. Also, as the top cuff 44 is preferably seamlessly formed by the inner shell 14, the border of the top opening 32 is smooth and configured to be gentle against the skin of the injured foot 100.

Figure 39:
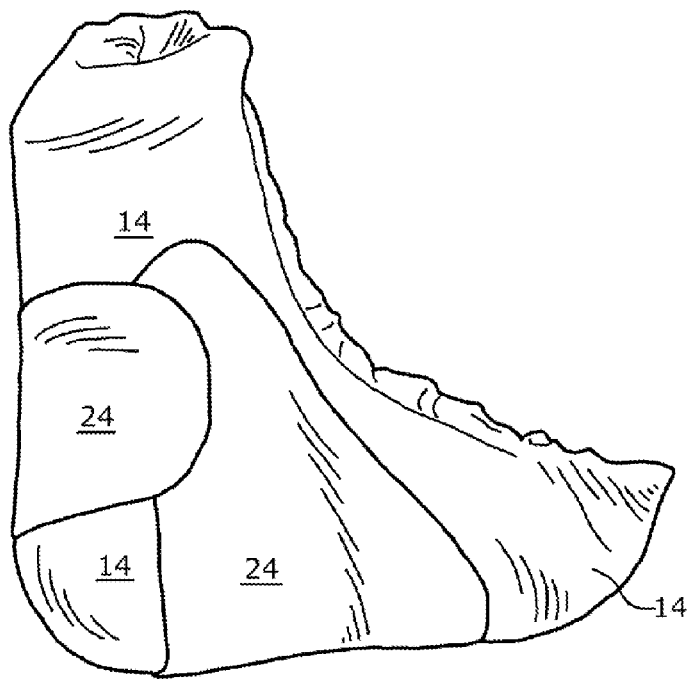
FIG. 39 is a right side perspective view following that shown in FIGS. 37 and 38 after attachment of structural supports during the construction of an ankle-foot orthosis.

Layered, in select locations, between the outer shell 12 and inner shell 14 are preferably structural supports 24 that are configured to rigidly support an injured area of the injured foot 100. For example, as shown in FIG. 39, in some embodiments, structural supports 24 are layered at locations configured to support the arch 40 area of an injured foot 100 and the Achilles tendon area of the injured foot 100, thereby providing behind-ankle support 36. Also preferably, in select locations between the exterior layer 18 and interior layer 20 of the pre-tibial shell 16 are structural supports 24. The structural supports 24 are configured to be less flexible than the outer shell 12 and inner shell 14. Accordingly, during use, as the outer shell 12, the inner shell 14, and pre-tibial shell 16 become worn and more flexible, the rigidity of the structural supports 24 decreases less than the rigidity of the leather decreases, thereby providing continued support to the injured areas of the injured foot 100 where the structural supports 24 are located between the outer shell 12 and inner shell 14 or between the exterior layer 18 and interior layer 20.

Figure 37:
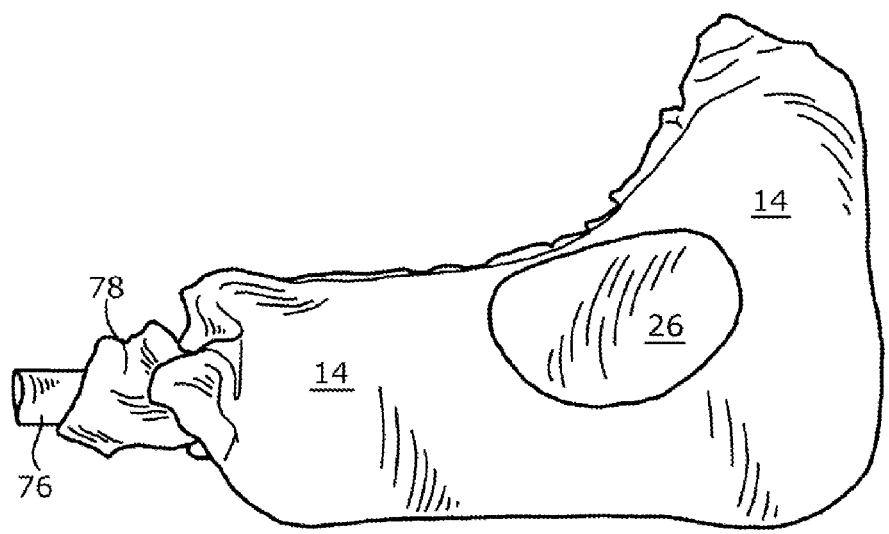
FIG. 37 is a right side perspective view following that shown in FIGS. 35 and 36 after attachment of padding during the construction of an ankle-foot orthosis.
Figure 38:
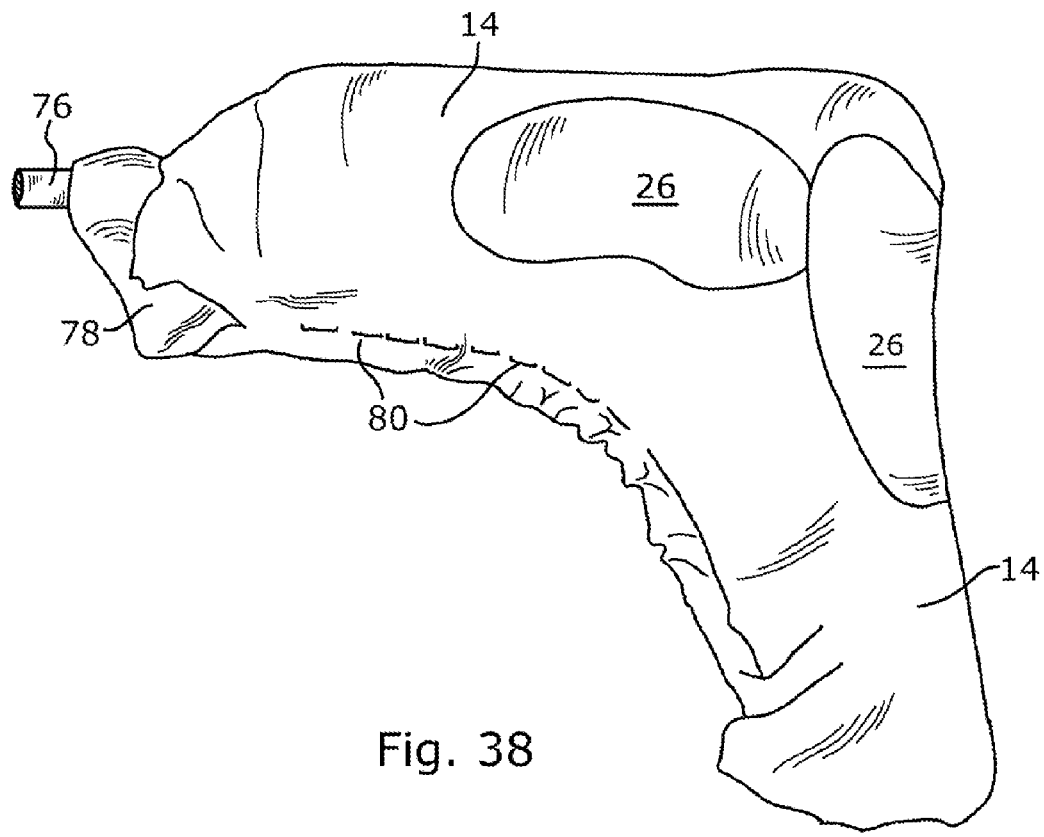
FIG. 38 is a left side perspective view of that shown in FIG. 37 during the construction of an ankle-foot orthosis.

Also, preferably, layered between the outer shell 12 and inner 14 are padding elements 26 that are configured to providing cushioning to select areas of the injured foot 100. For example, as shown in FIGS. 37 and 38, padding elements 26 are layered at locations configured to provide cushioning to the ankle bone and arch 40 areas of the injured foot 100. Likewise, preferably, in select locations between the exterior layer 18 and interior layer 20 of the pre-tibial shell 16 are located padding elements 26.

According to the depicted embodiments, the outer shell 12 and inner shell 14 are attached to one another via stitching 42. Likewise, the pre-tibial shell 16 is attached to the inner shell 14 via stitching 42. In other embodiments, the outer shell 12 and inner shell 14 are attached via adhesive without stitching 42 as is the pre-tibial shell 16 attached to the inner shell 14.

According to the depicted embodiments, upon first use of the ankle-foot orthosis 10, the ankle-foot orthosis 10 is essentially rigid and thus forms essentially a rigid cast that completely encompasses and surrounds the injured foot 100, providing circumferential control, except in the areas of the toes. Thus, even heel area 34 is enclosed by the injured foot 100. Through use, however, the outer shell 12, inner shell 14, and pre-tibial shell 16 wear and become more flexible, at least where no structural supports 24 are layered therebetween. Further, the use of the ankle-foot orthosis 10 over time and the resulting wear allows for natural tri-planar movement of the injured foot 100 because movement of the injured foot 100 in the natural tri-planar directions will inherently lead to increased flexibility in the ankle-foot orthosis 10 to accommodate such tri-planar movement. That is, over time and through use, the inner shell 14, outer shell 12, and pre-tibial shell 16 become more flexible, except in areas where the structural supports 24 are layered therebetween, such that the ankle-foot orthosis 10 allows for tri-planar flexing of the injured foot 100.

It is further preferred that the ankle-foot orthosis 10 include a closure device 22. According to the first embodiment, shown in FIG. 1, the closure device 22 comprises a system of eyelets and laces. With such a closure device 22, it is preferred that the laces used be of a color that is in contrast to the color of the outer shell 12, so as to make it easier for patients having poor eye-sight to visually distinguish the laces from the boot.

According to the second embodiment, shown in FIG. 2, the closure device 22 comprises a strap configured with hook and loop attachments. This second embodiment would be preferable for a patient that suffers from a hand joint disease such as rheumatoid arthritis. In either regard, the closure device 22 is configured to selectively reduce the width of the pre-tibial slit 48 by bringing the left inner edge 50 into closer proximity with the right inner edge 52 and by bringing the left outer edge 54 into closer proximity with the right outer edge 56 (FIG. 46). This secures the ankle-foot orthosis 10 to the injured foot 100. The closure device 22 is further configured to be selectively loosened, for accommodating doffing of the ankle-foot orthosis 10 by a patient, and tightened, for accommodating donning of the ankle-foot orthosis 10 by a patient.

The ankle-foot orthosis 10 is configured to be of a relatively low height, preferably approximately six inches in height for a patient of average adult height. The low height accommodates donning and doffing of the ankle-foot orthosis 10, makes the ankle-foot orthosis 10 cooler for the patient as compared to higher-height orthotics, and requires less packing space when the ankle-foot orthosis 10 is transported.

The ankle-foot orthosis 10 is configured to be relatively low weight. According to an embodiment configured for an adult patient weighing 160 pounds, it is preferred that the total weight of the ankle-foot orthosis 10 is fewer than 170 grams, so as to minimize the strain on the patient. In one such embodiment, the total weight of the ankle-foot orthosis 10 is only 157 grams. In any regard, preferable embodiments of the present ankle-foot orthosis 10 are more than 40% lighter in weight than traditional ankle-foot orthotics. After all, as little as an additional one hundred grams of weight on a foot can make a negative impact on the patient's heart. Further, the light-weight ankle-foot orthosis 10 decreases the risk that the patient wearing the ankle-foot orthosis 10 will trip or fall.

The construction of the boot of the ankle-foot orthosis 10 utilizing leather on the inner shell 14 and outer shell 12 minimizes the thickness of the boot. Thus, the ankle-foot orthosis 10 is configured to be worn by the patient in a shoe the patient wore prior to donning of the ankle-foot orthosis 10. That is, if the patient previously wore shoes properly fitted using a weight-bearing measurement taken with a properly-calibrated Brannock device, at least in some embodiments, the patient will be able to wear the ankle-foot orthosis 10 in this same shoe. Accordingly, the patient need not buy new shoes to accommodate the ankle-foot orthosis 10 and need not wear one large shoe on the foot wearing the ankle-foot orthosis 10 and one smaller shoe on a foot not wearing an orthosis.

The Figures also show depictions of an ankle-foot orthosis 10 during the construction thereof. As shown in FIG. 10, the method for constructing the ankle-foot orthosis 10 begins with the injured foot 100, for which the ankle-foot orthosis 10 is to be custom molded. The injured foot 100 is put in a non-weight-bearing position. Then, taping 60 is applied to the injured foot 100 to encourage the injured foot 100 into a first corrected position wherein the second toe of the injured foot 100 is in alignment with the midline of the patient's kneecap. Preferably, the taping 60 is applied to put the injured foot 100 into a configuration best for addressing the condition of the injured foot 100 to be treated. For example, as shown in FIG. 11, in a first taping configuration, the taping 60 is applied to the injured foot 100 across the large toe so as to address a low arch condition of the injured foot 100. As another example, as shown in FIGS. 12 and 13, in a second taping configuration, the taping 60 is applied to the injured foot 100 across the heel area and then also the arch area so as to address an overall collapsing foot condition so as to put the arch into a neutral position. As another example, shown in FIG. 14, in a third taping configuration, the taping 60 is applied tightly across the talonavicular joint area to address an injured foot 100 that otherwise has a sag in that area. As another example, shown in FIG. 15, in a fourth taping configuration, the taping 60 is applied from the outside of the heel across to the inside of the heel to address an injured foot 100 that is otherwise held by the patient in an outwardly-turned position, i.e., in valgus configuration. As another example, shown in FIG. 16, in a fifth taping configuration, the taping 60 is applied from the inside of the heel across to the outside of the heel to address an injured foot 100 that is otherwise held by the patient in an inwardly-turned position, i.e., in varus configuration. This taping step, therefore, is the first opportunity to correct the condition of the injured foot 100 to be treated.

Figure 17:
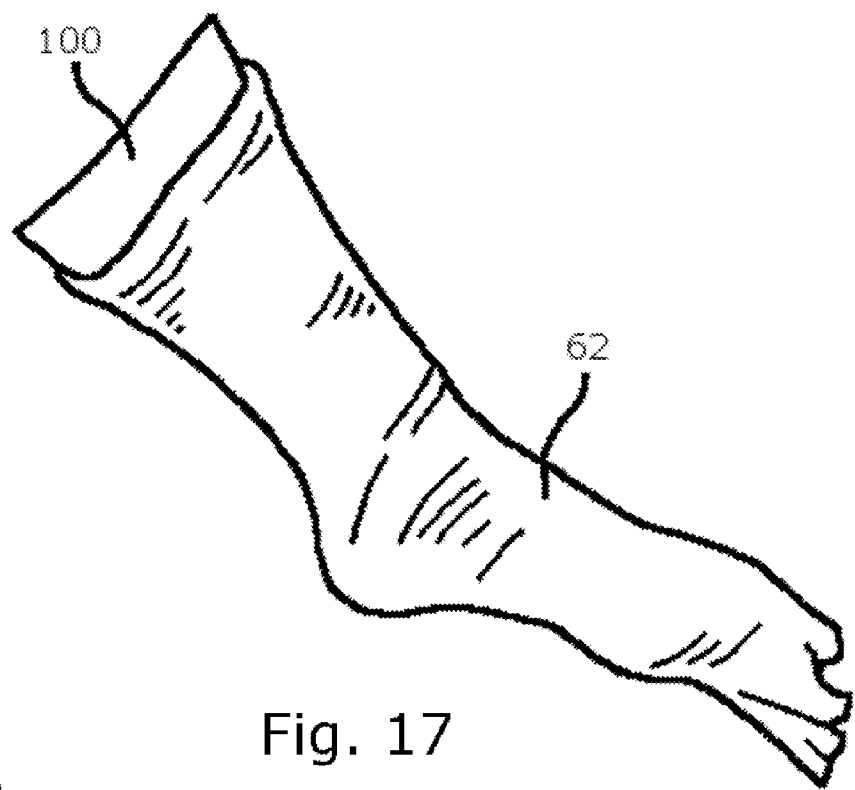
FIG. 17 is a right side elevation view of an injured foot taped and inserted within a stockinet sock during the construction of an ankle-foot orthosis.
Figure 18:
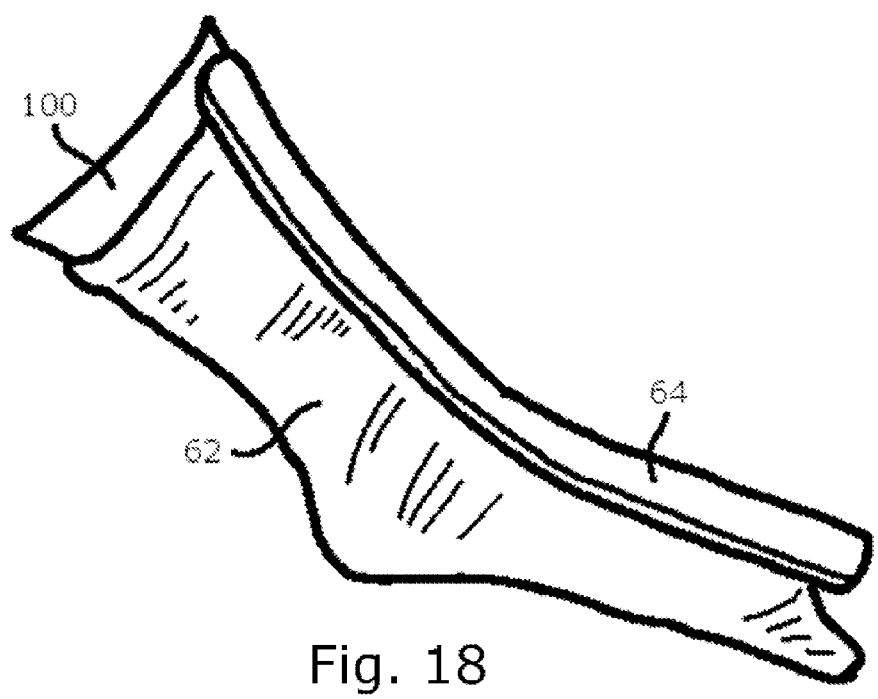
FIG. 18 is a right side elevation view following that shown in FIG. 17 with a splint put in place during the construction of an ankle-foot orthosis.

Following the taping, as shown in FIG. 17, the taped injured foot 100 is inserted into a stockinet sock 62, again while the injured foot 100 is in a non-weight-bearing position, i.e., while the patient's weight is not bearing upon the injured foot 100. Then, as shown in FIG. 18, a padded aluminum splint 64 is placed along a front portion of the injured foot 100 extending from the patient's toes to the patient's shin. The front portion is preferably that proximate to the injured foot 100's pre-tibial region. Preferably, the padded aluminum splint 64 includes an aluminum strip top layer attached to a padding strip lower layer, where the padding strip lower layer is configured to rest against the front portion of the injured foot 100, as shown in FIGS. 18 through 22.

Figure 19:
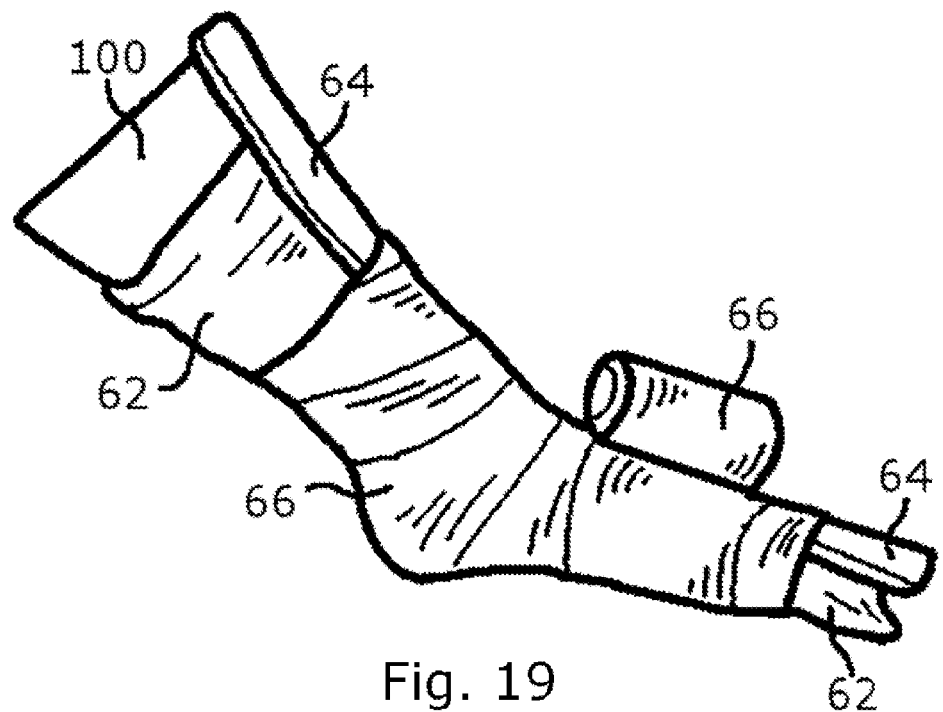
FIG. 19 is a right side elevation view following that shown in FIG. 18 during wrapping with casting material during the construction of an ankle-foot orthosis.
Figure 20:
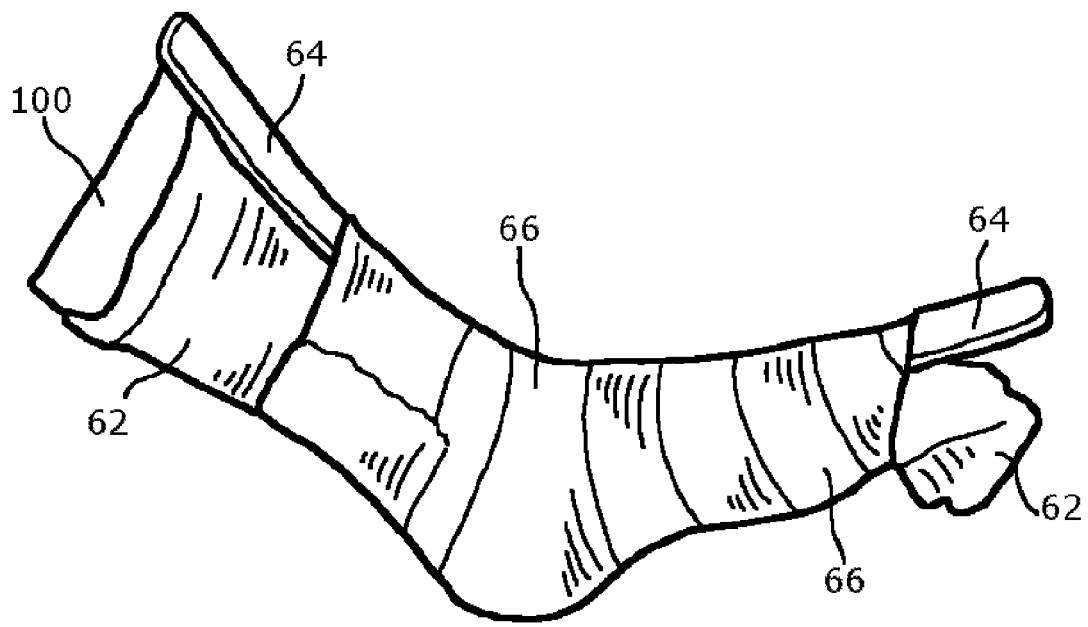
FIG. 20 is a right side elevation view following that shown in FIG. 19 after wrapping with the casting material during the construction of an ankle-foot orthosis.
Figure 21:
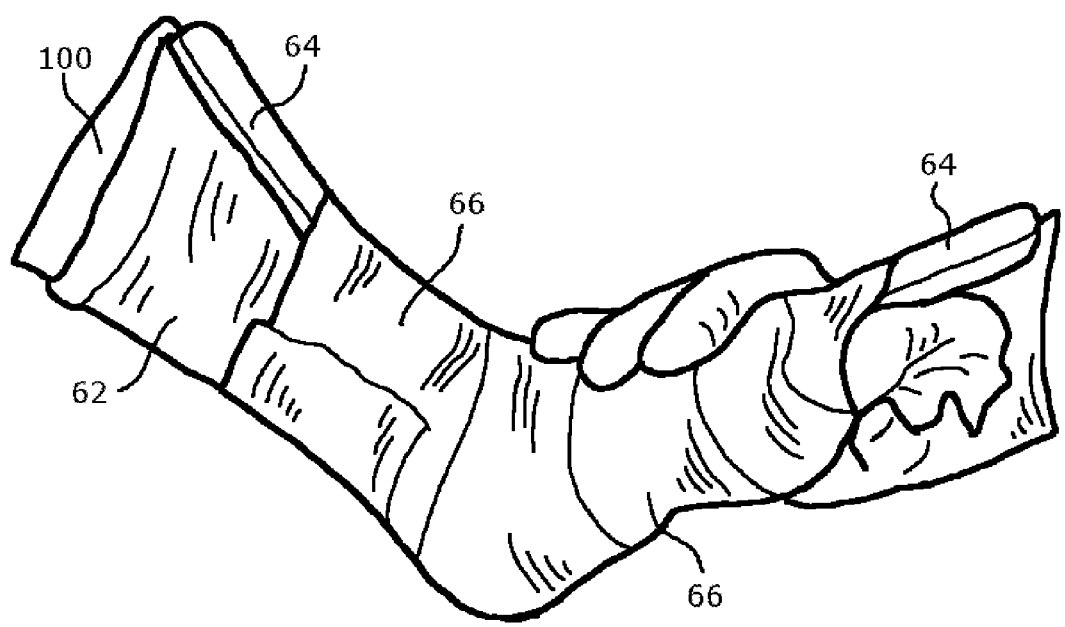
FIG. 21 is a top and right side perspective view following that shown in FIG. 20 during positioning to a second corrected position during the construction of an ankle-foot orthosis.

As shown in FIG. 19, the injured foot 100 in the stockinet sock 62 and the padded aluminum splint 64 are then wrapped with a hardening casting material, such as fiberglass casting material 66. The casting material 66 is wrapped so as to surround a majority of the injured foot 100 without surrounding the patient's toes or upper calf, as shown in FIG. 20. As shown in FIG. 21, as the hardening casting material 66 is allowed to harden, the injured foot 100 is dorsiflexed into a second corrected position wherein the injured foot 100 and the patient's shin form an angle in the range of seventy to one-hundred ten degrees. Preferably, the injured foot 100 is dorsiflexed to a second corrected position wherein the injured foot 100 and the patient's shin form an angle of ninety degrees.

While dorsiflexing the injured foot 100 into the second corrected position or thereafter, the injured foot 100 is further placed into a third corrected position wherein the injured foot 100 is in a subtalar neutral position. Once placed in the third corrected position, the casting material 66 is molded or smoothed along the injured foot 100 to conform the casting material 66 to the shape of the injured foot 100 in the third corrected position. The casting material 66 is then allowed to complete its hardening.

Figure 22:
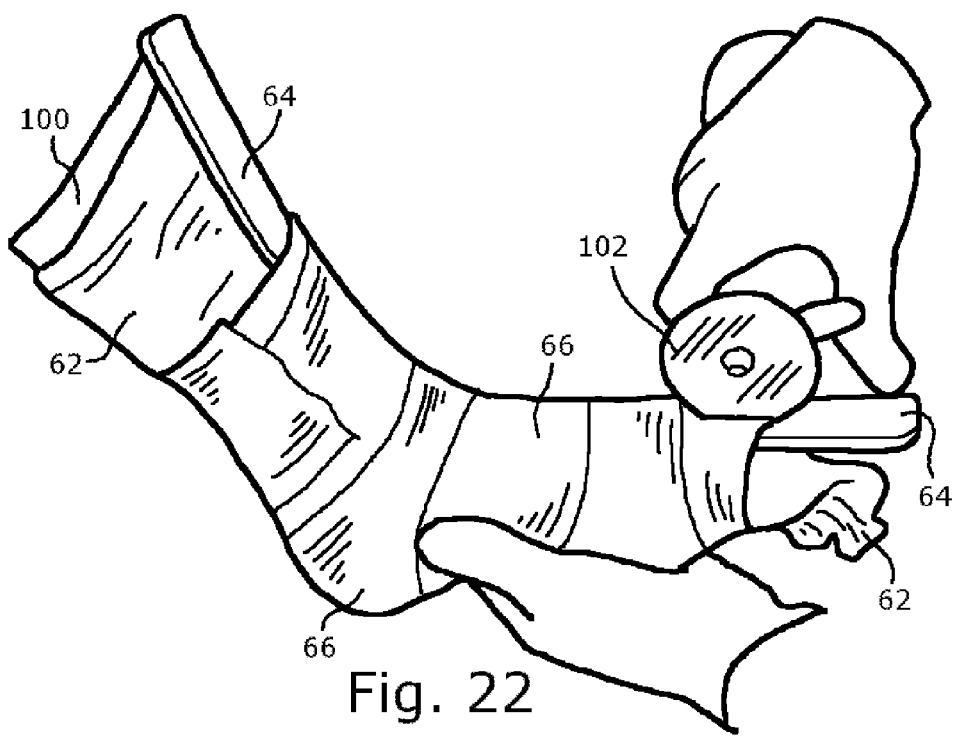
FIG. 22 is a top and right side perspective view following that shown in FIG. 21 during cutting of the casting material during the construction of an ankle-foot orthosis.
Figure 23:
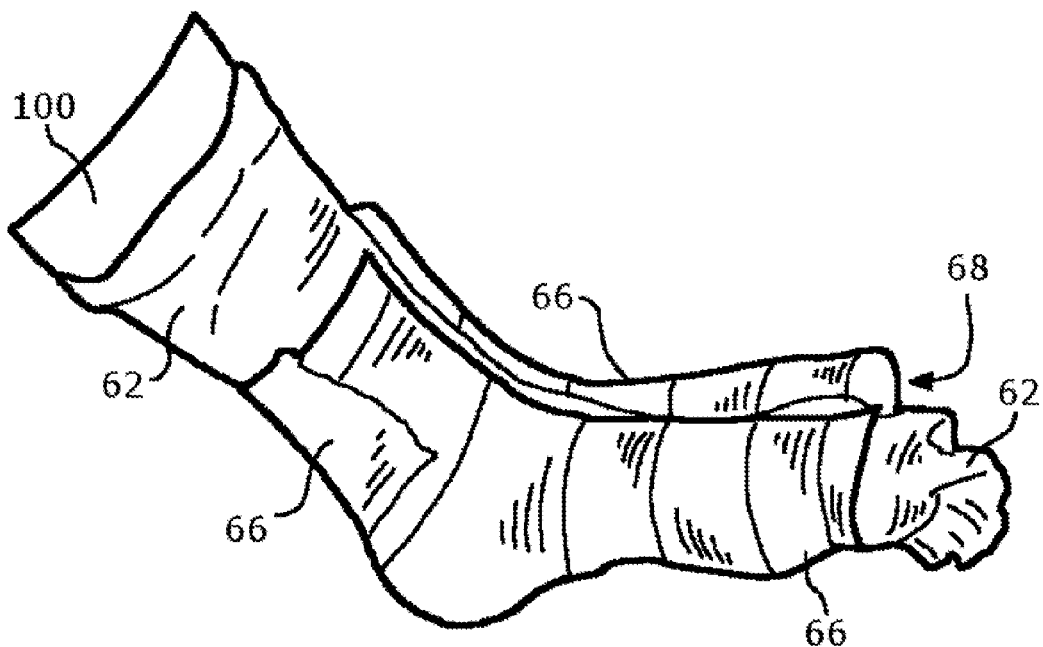
FIG. 23 is a top and right side perspective view following that shown in FIG. 22 after cutting of the casting material during the construction of an ankle-foot orthosis.
Figure 24:
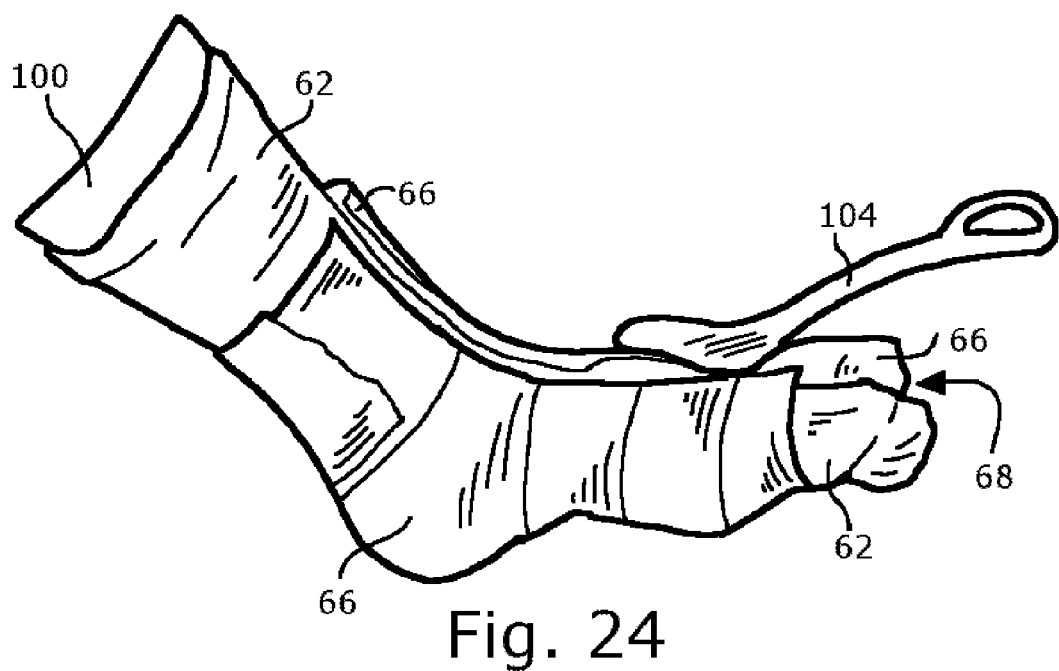
FIG. 24 is a top and right side perspective view following that shown in FIG. 23 during cutting of the stockinet sock during the construction of an ankle-foot orthosis.

As shown in FIG. 22, once the hardening casting material 66 is hardened, a saw 102 is used to cut the stiffened casting material 66 along the padded aluminum splint 64 so as to form a slit 68 shown in FIG. 23. The padded aluminum splint 64 plays its part during the cutting to protect the injured foot 100 from the saw 102. The padded aluminum splint 64 further blocks the saw 102 from cutting the stockinet sock 62. Once the casting material 66 is cut to form the slit 68, the padded aluminum splint 64 is removed via the slit 68. As shown in FIG. 24, scissors 104 are then used to cut the stockinet sock 62 along the slit 68. The stockinet sock 62 and stiffened casting material 66 are then removed from the injured foot 100. As shown in FIG. 25, the now-stiffened casting material 66 forms a negative cast having a shape of the injured foot 100 in the third corrected position. As shown in FIG. 26, the stockinet sock 62 is then separated away from the stiffened casting material 66 so as to leave just the negative cast formed by the now-stiffened casting material 66.

Figure 27:
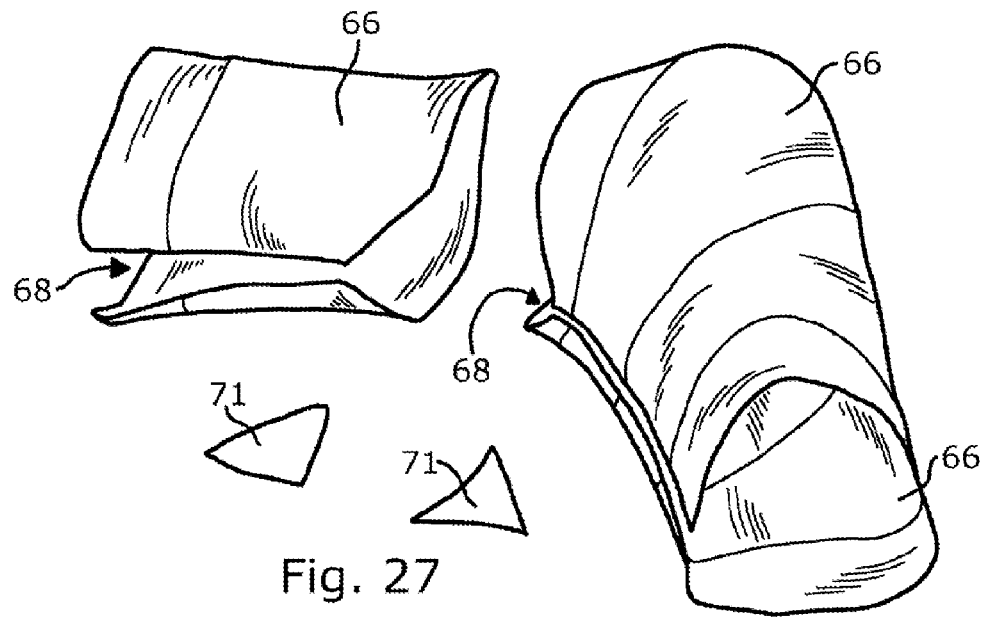
FIG. 27 is a left side perspective view following that shown in FIG. 26 after cutting along a cut line during the construction of an ankle-foot orthosis.

In some embodiments, the method for construction also includes the steps of cutting the negative cast and reforming the negative cast into another corrected position. For example, as shown in FIG. 26, the negative cast of the stiffened casting material 66 is marked with a cut line 70. The negative cast of the stiffened casting material 66 is then cut along the cut line 70, as shown in FIG. 27. Thereafter, the upper-most portion and the lower-most portion of the cut negative cast are rejoined in another corrected position, such as one in which the upper-most portion and lower-most portion are in a narrower angle relative to one another. According to the embodiment shown in FIG. 27, cutaway portions 71 of the original negative cast are removed to accommodate the realignment of the upper-most portion and the lower-most portion in the narrower angle. In other embodiments, the upper-most portion and the lower-most portion are rejoined in another corrected position in which the upper-most portion and the lower-most portion are in a wider angle relative to one another. These steps of adjusting the position of the negative cast by cutting and realigning the upper and lower portions thereof are useful in constructing an ankle-foot orthosis 10 that is to be used for a patient who was not physically able to withstand positioning of his or her injured foot 100 into the proper corrected position, either of a narrower or wider angle, as the case may be, prior to the wrapping with the casting material 66. With these steps, therefore, even before a mold is created, position corrections are made during the pre-taping steps, during the casting itself, and, in some embodiments, to the negative cast itself.

Figure 28:
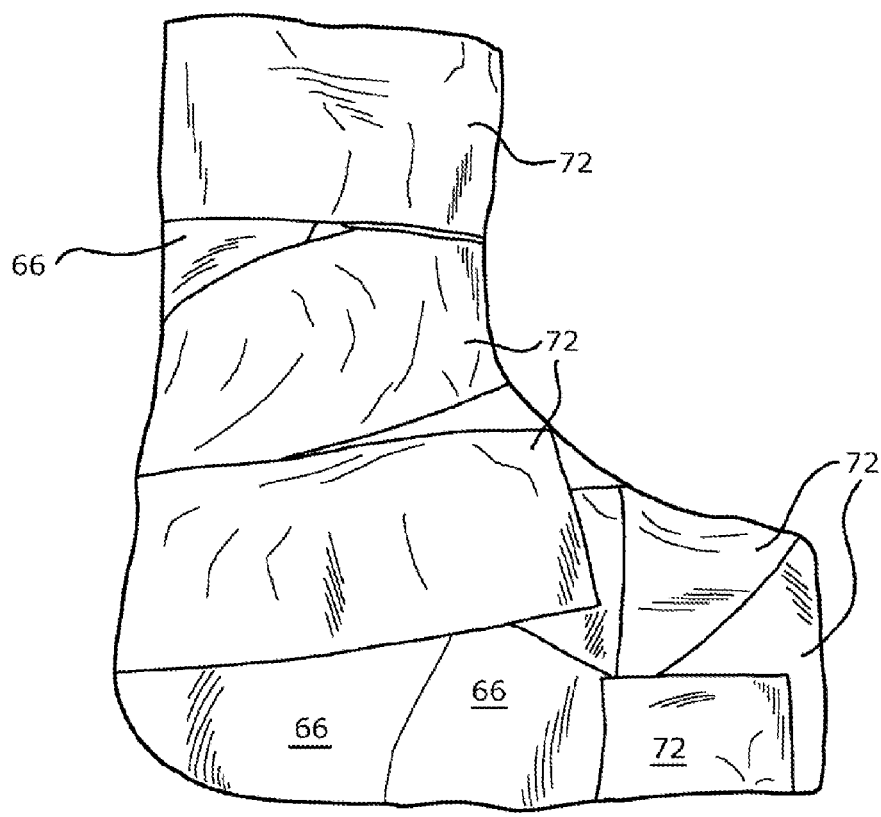
FIG. 28 is a right side elevation, perspective view following that shown in FIG. 27 after wrapping the negative cast with sealing tape during the construction of an ankle-foot orthosis.
Figure 29:
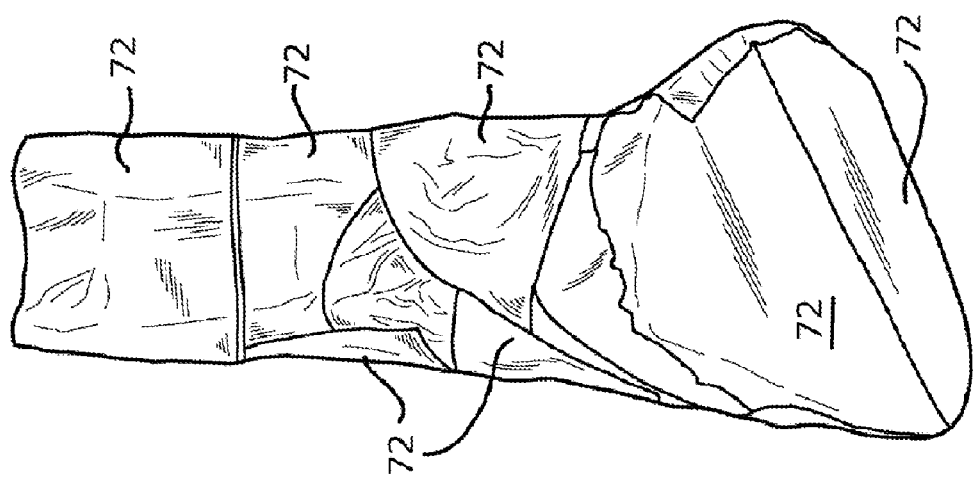
FIG. 29 is a front elevation, perspective view of that shown in FIG. 28 during the construction of an ankle-foot orthosis.

As shown in FIGS. 28 and 29, the negative cast, whether reformed as described above or not reformed, is preferably largely wrapped with sealing tape 72 so as to close off large open areas, such as the large opening created by the toes section of the injured foot 100 during casting. In some embodiments, sealing tape 72 wraps all of the negative cast, with the exception of the upper-most opening, i.e., that created by the ankle of the patient during casting.

Figure 30:
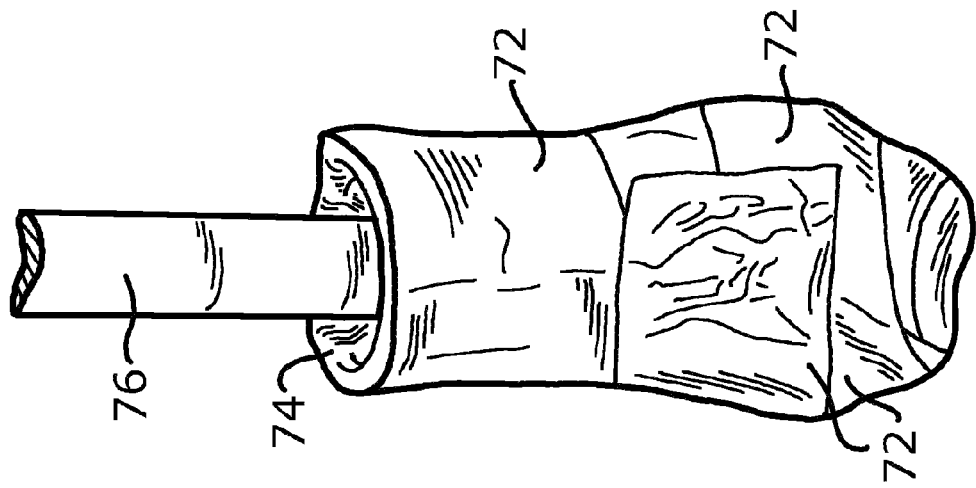
FIG. 30 is a partial, top and front side perspective view following that shown in FIGS. 28 and 29 after pouring of hardening fluid into the negative cast to form a mold during the construction of an ankle-foot orthosis.
Figure 31:
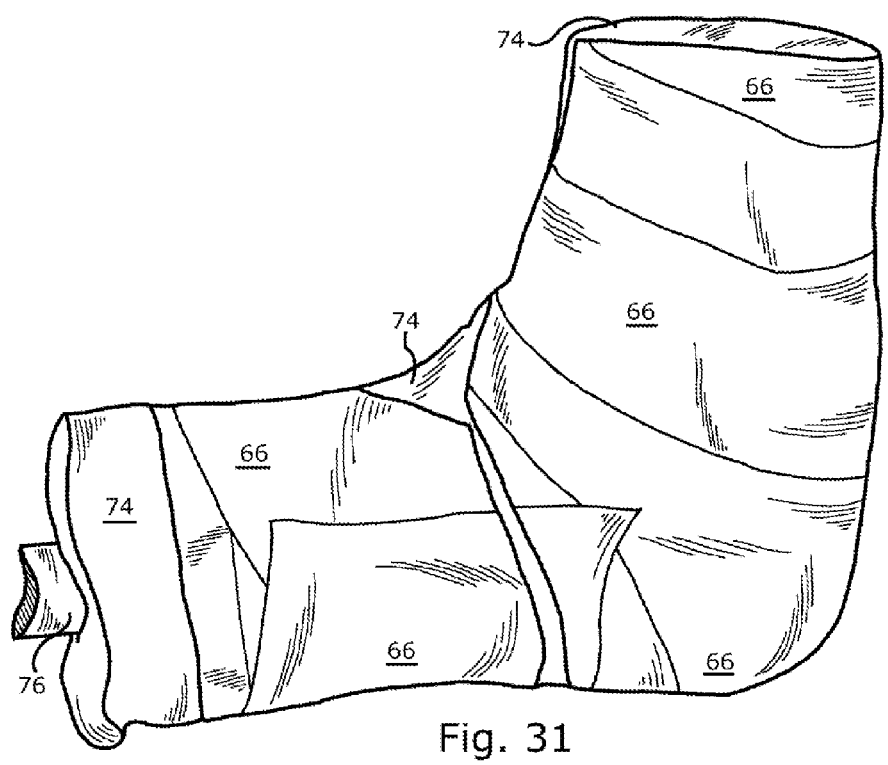
FIG. 31 is a right side elevation, perspective view following that shown in FIG. 30 during the construction of an ankle-foot orthosis.
Figure 32:
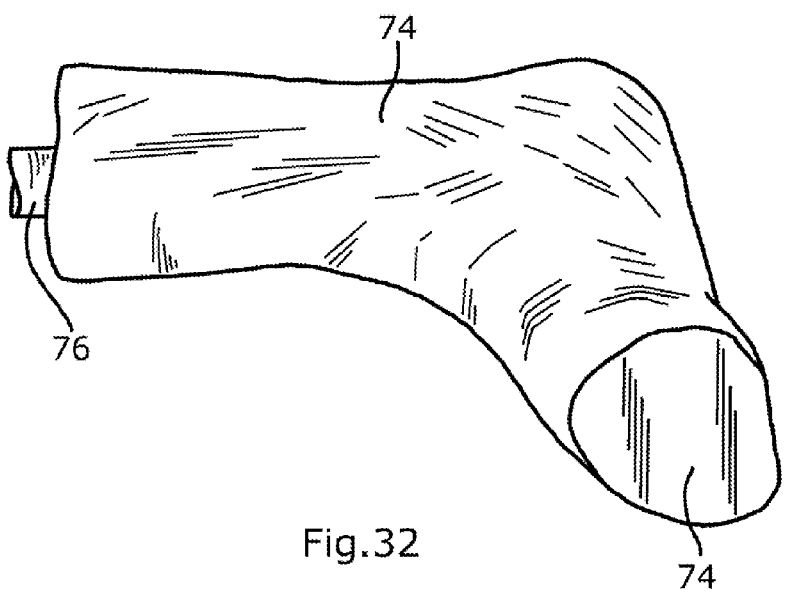
FIG. 32 is a front and left side perspective view following that shown in FIG. 31 after removal of the negative cast from and filing of the mold during the construction of an ankle-foot orthosis.

As shown in FIG. 30, a rod 76 is then at least partially inserted into the negative cast of the stiffened casting material 66 and hardening fluid 74 is poured into the remaining space of the negative cast. In some embodiments, the rod 76 comprises a galvanized pipe with a flattened end, which is inserted into the negative mold. The inclusion of the rod 76 accommodates bracing or stabilization of the mold during later steps in the construction process. In some embodiments, the hardening fluid 74 used is a hardening plaster. In such embodiments, it is preferred that a release agent be added to the negative cast before the hardening fluid 74 is poured therein. (The release agent is configured to accommodate removal of the negative mold from the eventually-hardened hardening fluid 74.) The hardening fluid 74 is allowed to harden such that the hardening fluid 74 forms a mold. Thereafter, any sealing tape 72 is removed, leaving the mold of the hardened hardening fluid 74 within the negative cast of the stiffened casting material 66, as shown in FIG. 31. The negative cast of the casting material 66 is then separated from the mold. As shown in FIG. 32, the mold is then filed to remove any excess hardening fluid 74 that may have protruded into open areas of the negative cast. Thereafter, in some embodiments, additional hardening fluid 74 is applied in relatively small amounts to smooth areas of the mold or to build up areas of the mold, such as the ankle-bone area or the heel area, to allow for extra space in those areas once the mold is used. During this step, therefore, additional shape or position corrections can be made.

Figure 33:
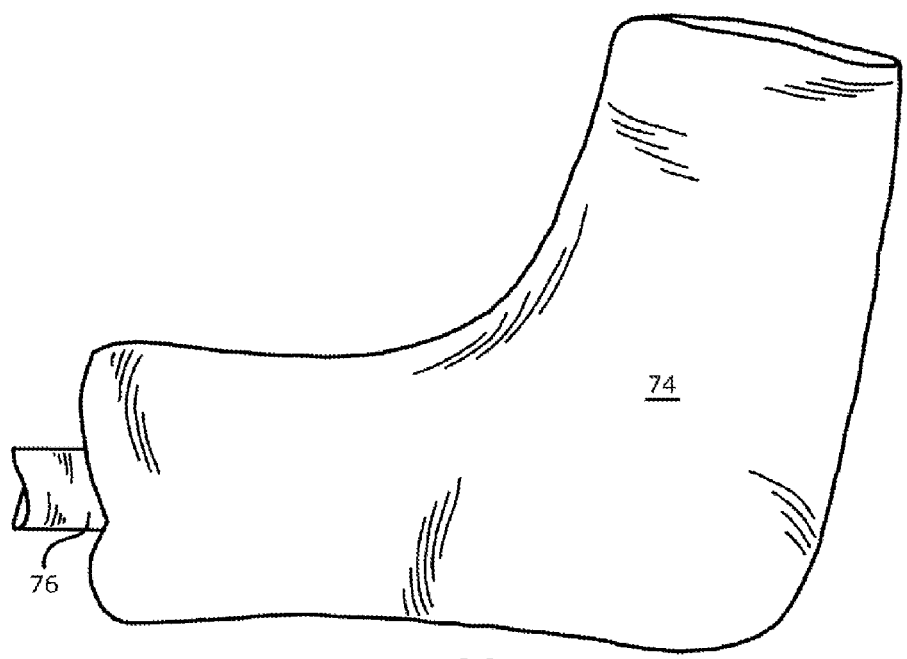
FIG. 33 is a right side elevation, perspective view following that shown in FIG. 32 after smoothing of the mold during the construction of an ankle-foot orthosis.
Figure 34:
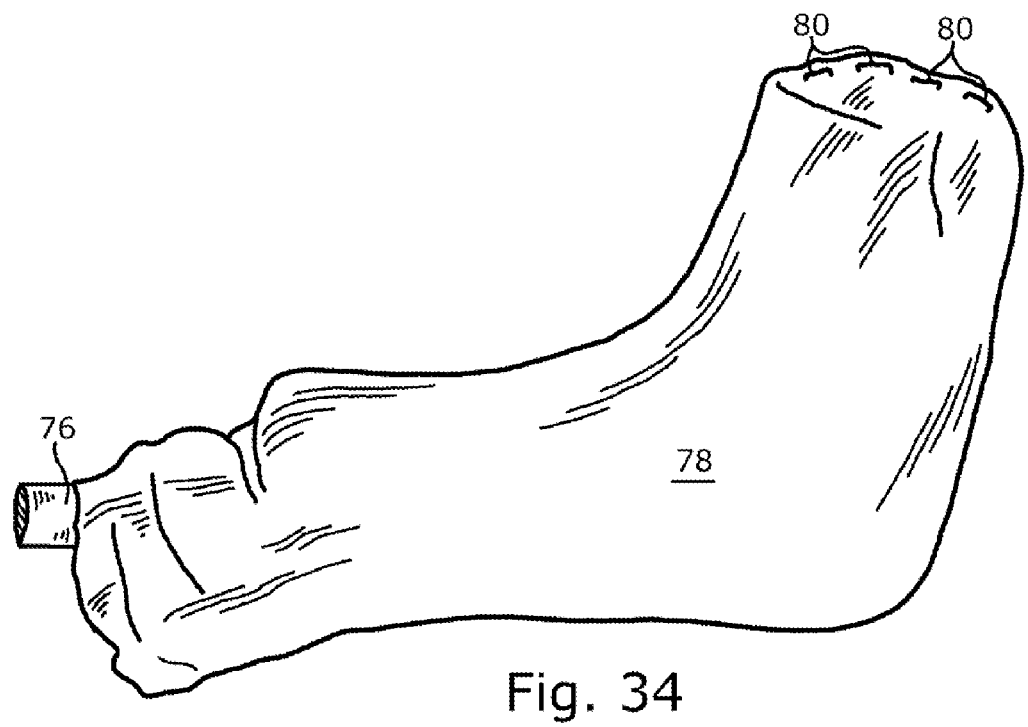
FIG. 34 is a right side perspective view following that shown in FIG. 33 after covering the mold with a liner during the construction of an ankle-foot orthosis.

The resulting smoothed mold, as shown in FIG. 33, is then covered with a liner 78, preferably a cloth liner 78, as shown in FIG. 34. In some embodiments, the liner 78 is affixed to the mold via temporary fasteners 80, such as staples, nails, screws, tacks, or the like. In other embodiments, the liner 78 is permanently affixed to the mold. Because the mold of hardened hardening fluid 74 is covered with a liner 78, the resulting ankle-foot orthosis 10 will be configured to accommodate an injured foot 100 that is wearing a sock or stocking.

Figure 35:
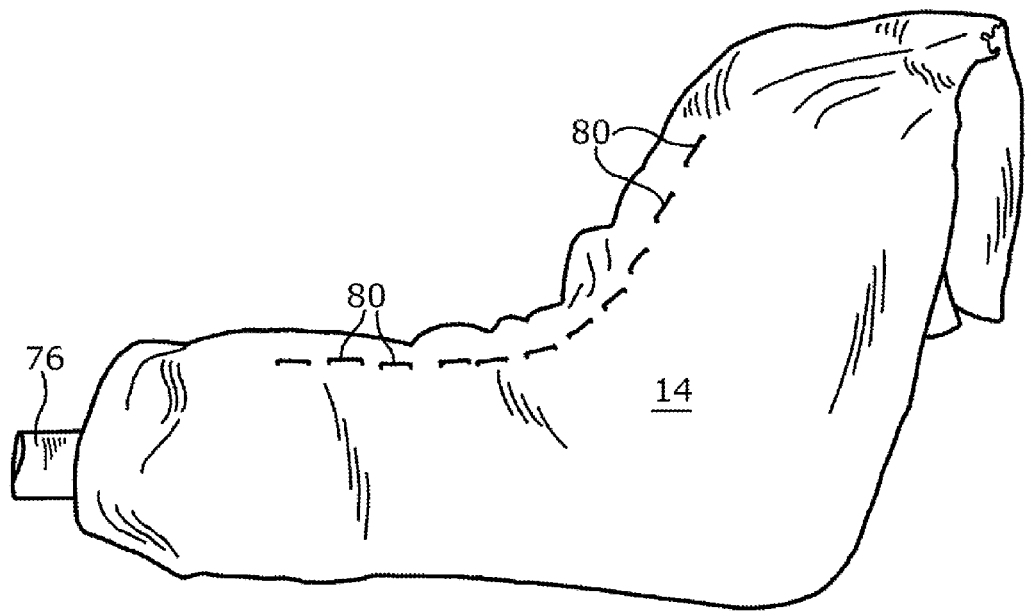
FIG. 35 is a right side perspective view following that shown in FIG. 34 after stretch molding of an inner shell during the construction of an ankle-foot orthosis.
Figure 36:
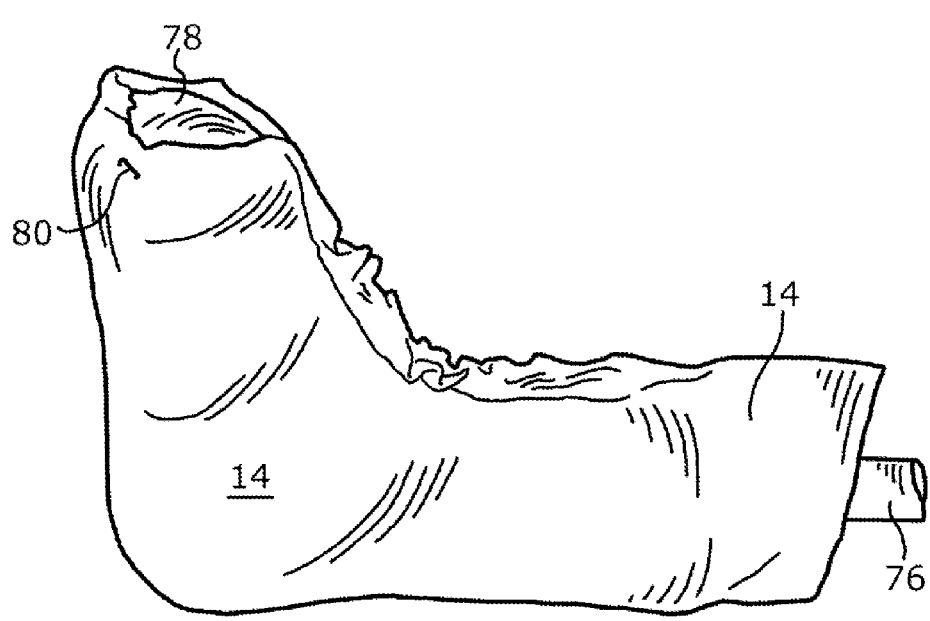
FIG. 36 is left side a left side perspective view of that shown in FIG. 35 during the construction of an ankle-foot orthosis.

Next, a boot is molded to the liner 78 lined mold. This is accomplished by stretch molding a seamless leather inner shell 14 over the mold. In some embodiments, the inner shell 14 is affixed to the mold and liner 78 via temporary fasteners 80, as shown in FIGS. 35 and 36. Preferably, the leather used for the inner shell 14 will be stretch molded over the mold so that the smooth side of the leather is next to the liner 78, leaving the rough side exposed.

Thereafter, padding elements 26 are adhered to the exposed side of the inner shell 14 at select padding areas. For example, as shown in FIGS. 37 and 38, padding elements 26 are added to cushion select padding areas of the ankle bone and lower heel areas of the injured foot 100. The number of padding elements 26 adhered, the thickness of the padding elements 26 adhered, and the select padding areas to which the padding elements 26 are adhered are chosen based on the needs of the patient, such as the patient's condition, weight, and activity level. Thus, in other embodiments, padding elements 26 are alternatively placed in the area of the navicular bone or the arch. Further, in some embodiments, the padding elements 26 are adhered to the select padding areas via epoxy, glue, tape, or other adhesive. In other embodiments, the padding elements 26 are adhered to the select padding areas via lamination, either in one layer or in multiple layers. In embodiments utilizing layers of padding elements 26, the thickness of the layers is not necessarily equal. Padding elements 26 used are preferably padding elements comprising any of ethylene vinyl acetate, microcellular polyurethane, closed-cell cross-linked polyethylene, and fine-cell polyethylene. Padding elements 26 applied via lamination are preferably soft leather or foam padding having a durometer between fifteen and eighty-five.

Following addition of padding elements 26 to the inner shell 14, structural supports 24 are selectively adhered to the inner shell 14 in selective stiffener areas. For example, as shown in FIG. 39, structural supports 24 are added to the arch and Achilles tendon areas. According to this embodiment, the structural support 24 in the Achilles tendon area does not pass up to the top of the ankle-foot orthosis 10, which allows the patient to have a more normal gait while wearing the ankle-foot orthosis 10. In other embodiments, structural supports 24 are alternatively adhered just to the arch area or to the navicular bone area. The selective stiffener areas chosen are those areas at which the most limitation on movement is desired.

In some embodiments, the structural supports 24 are added on top of padding elements 26 already added. However, in other embodiments, the structural supports 24 are added directly against the inner shell 14. As with the padding elements 26, the number of structural supports 24 adhered, the thickness of the structural supports 24 adhered, the relative rigidity or flexibility of the structural supports 24 adhered, and the selective stiffener areas to which the structural supports 24 are adhered are chosen based on the needs of the patient and the patient's condition, such as the patient's weight, diagnosis, and activity level. Further, in some embodiments, the structural supports 24 are adhered to the selective stiffener areas via epoxy, glue, tape, or other adhesive. In other embodiments, the structural supports 24 are adhered to the selective stiffener areas via lamination, either in one layer or in multiple layers. Such laminate structural supports 24 are preferably composed of heat-moldable thermoplastic, such as polypropylene that is configured to be applied in multiple layers each of one millimeter thickness. In the embodiments utilizing such laminate structural supports 24, the structural supports 24 can be adhered at selective stiffener areas configured to address any of a number of foot conditions, such as heel varus, heel valgus, forefoot varus, forefoot valgus, talonavicular joint issues, spring ligament issues, and calcaneal cuboid joint issues.

Figure 40:
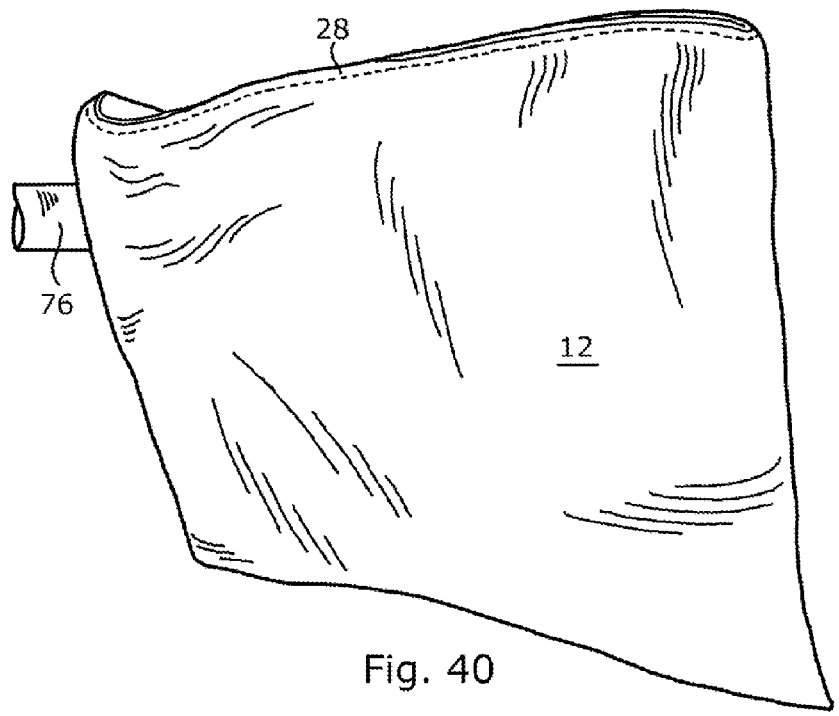
FIG. 40 is a left side perspective view following that shown in FIG. 39 during stretch molding of an outer shell during the construction of an ankle-foot orthosis.
Figures 41, 42:
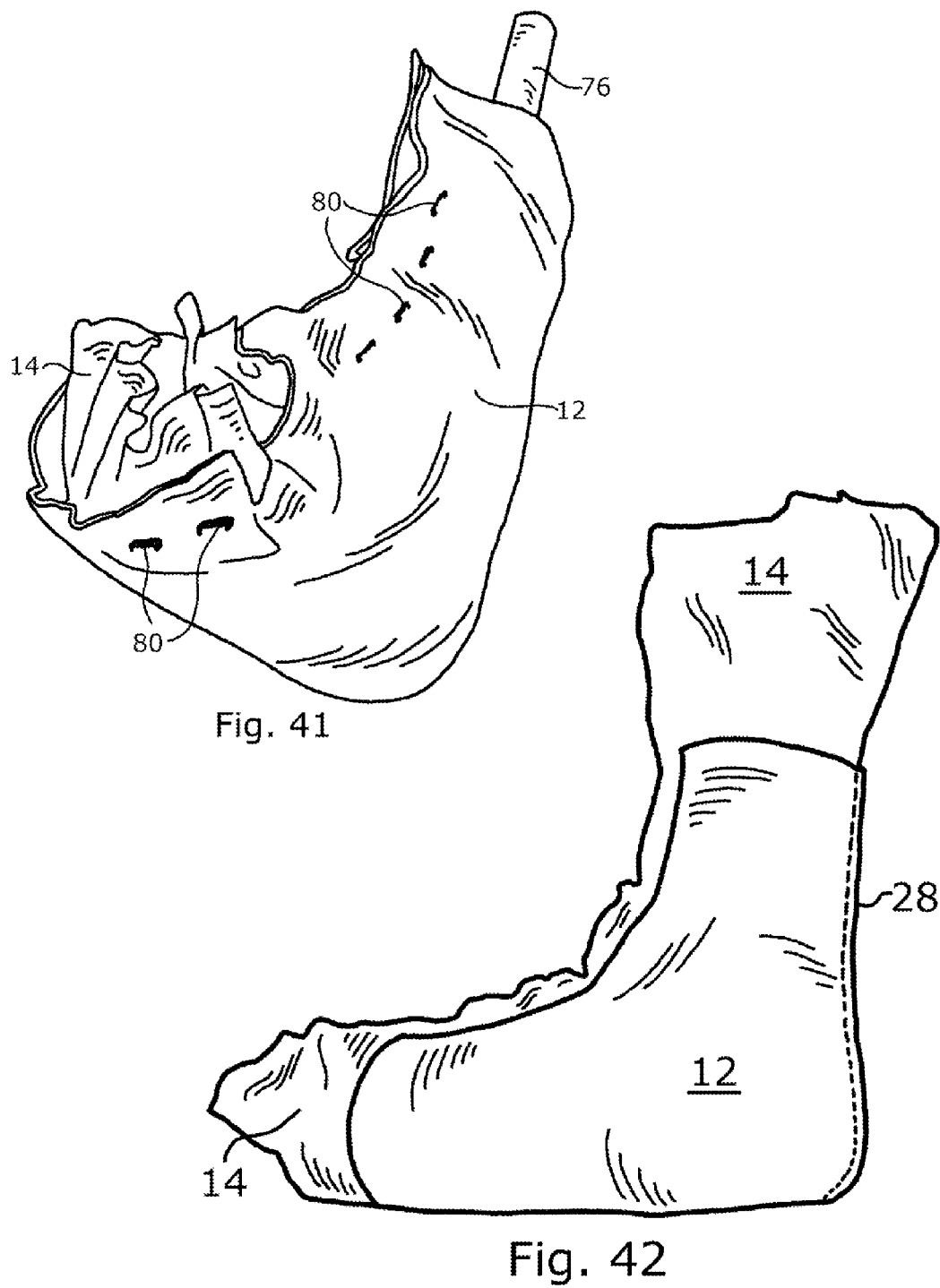
FIG. 41 is a front, left, and bottom side perspective view following that shown in FIG. 40 after stretch molding of the outer shell during the construction of an ankle-foot orthosis.
FIG. 42 is a left side elevation view following that shown in FIG. 41 after trimming of the outer shell during the construction of an ankle-foot orthosis.
Figure 43:
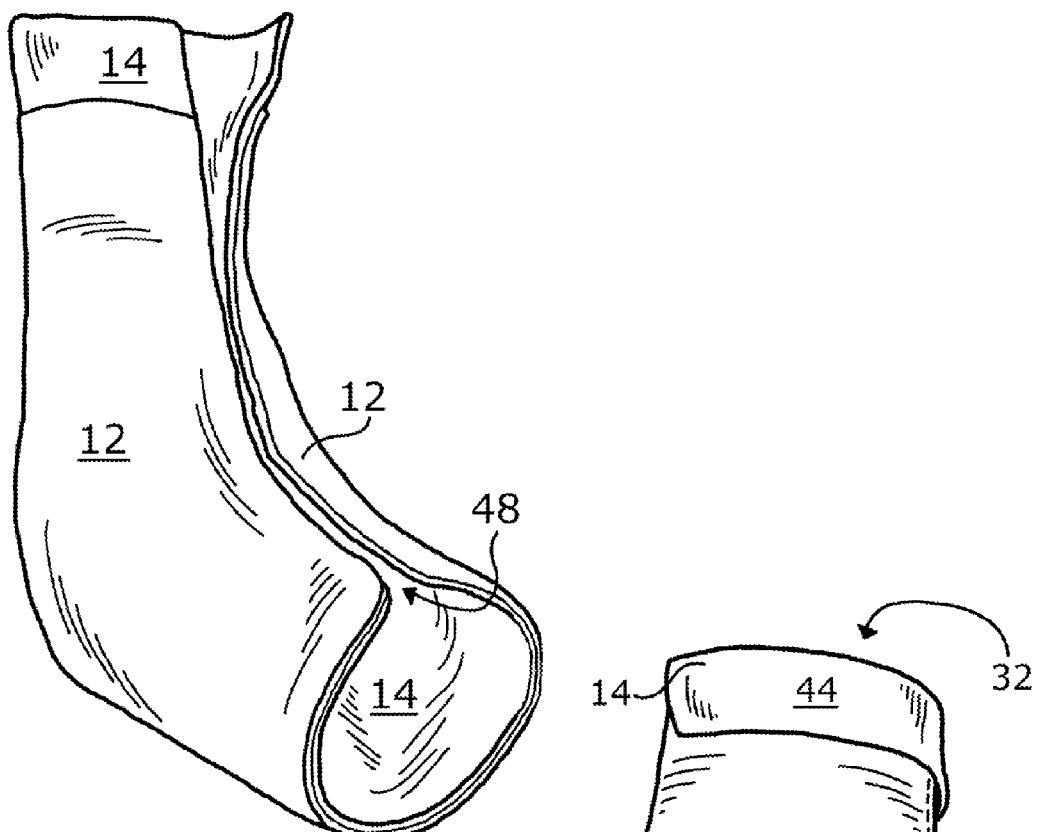
FIG. 43 is a front and right side perspective view following that shown in FIG. 42 after trimming of the inner shell during the construction of an ankle-foot orthosis.
Figure 44:
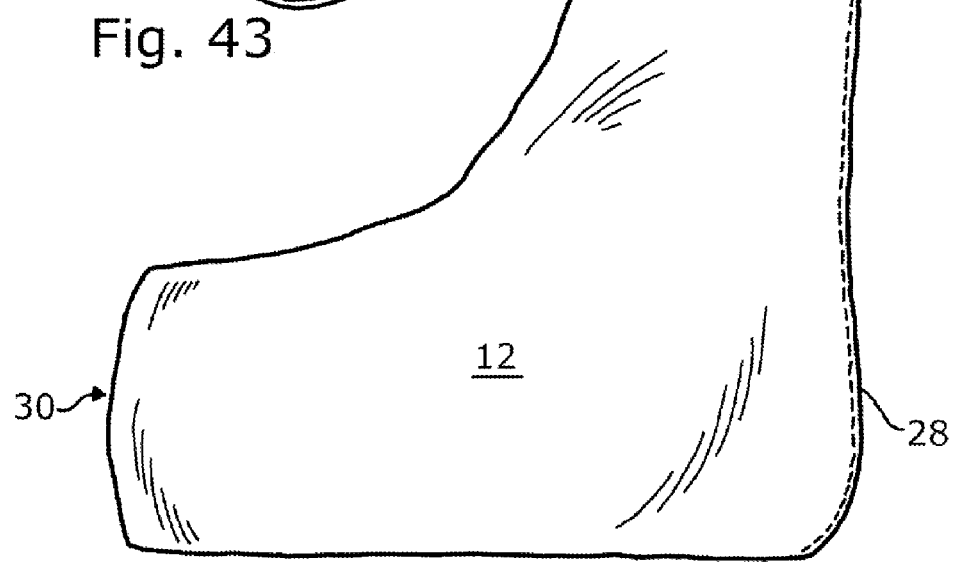
FIG. 44 is a left side elevation view following that shown in FIG. 43 after forming a top cuff during the construction of an ankle-foot orthosis.

Thereafter, as shown in FIG. 40, an outer shell 12 is stretch molded over the inner shell 14, padding elements 26, and structural supports 24. Preferably the outer shell 12 includes only one seam 28 that is arranged to be located in the rear area of the ankle-foot orthosis 10. Also, preferably, after stretch molding of the outer shell 12, it is affixed in its molded position via temporary fasteners 80, as shown in FIG. 41, and then selectively stiffened in total and/or in specific locations, according to the needs of the patient. In some embodiments, the leather is selectively stiffened using an alcohol solution. The amount of alcohol used in the solution is chosen based on the desired rigidity at the specific location. Once stiffened, the excess of the outer shell 12 is trimmed away from the areas of what will become the top opening 32, front opening 30, left outer edge 54, and right outer edge 56 (see FIG. 46), as shown in FIG. 42. Thereafter, as shown in FIG. 43, excess of the inner shell 14 is trimmed away to align with the outer shell 12 at the areas of the front opening 30 and the pre-tibial slit 48. This leaves the left inner edge 50 aligned with the left outer edge 54 and the right inner edge 52 aligned with the right outer edge 56. Preferably, the uppermost edge of the inner shell 14 is not trimmed to align with the uppermost edge of the outer shell 12. Rather, as shown in FIG. 43, the inner shell 14 is trimmed so that a portion extends upward and away from the outer shell 12. This top portion of the inner shell 14 is then folded down so that the top portion of the inner shell 14 overlaps a top portion of the outer shell 12 in a region proximate to the front opening 30, forming a top cuff 44, as shown in FIG. 44.

Figure 45:
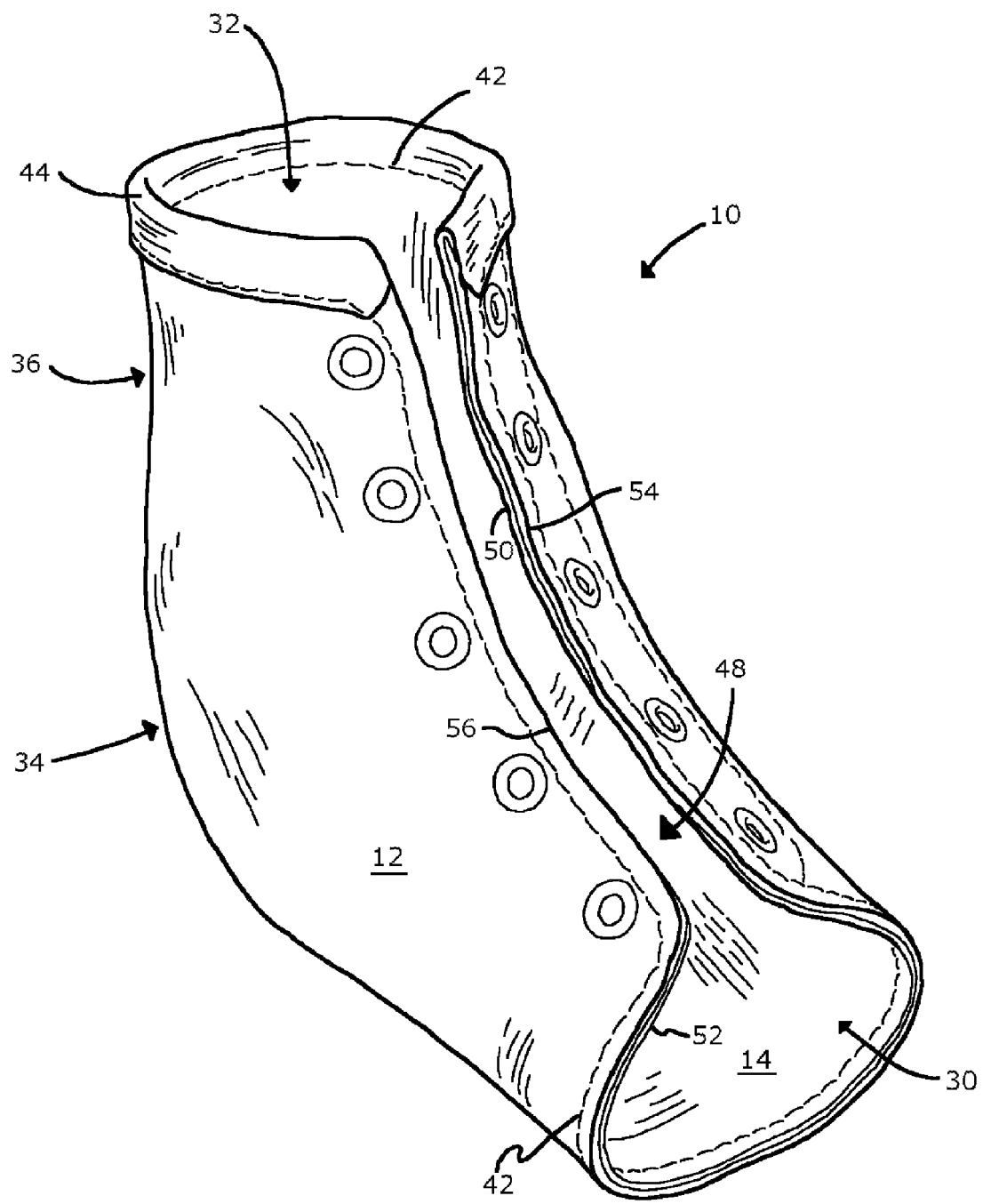
FIG. 45 is a front and right side perspective view following that shown in FIG. 44 after affixing the inner shell and outer shell together and formation of eyelets of a closure device during the construction of an ankle-foot orthosis.

Preferably, the outer shell 12 and inner shell 14 are thereafter affixed to one another so as to prevent the outer shell 12 and inner shell 14 from shifting undesirably relative to one another. According to the embodiment depicted in FIG. 45, the outer shell 12 and inner shell 14 are affixed to one another via stitching 42. The stitching 42 is configured to be minimally intrusive upon an injured foot 100 wearing the ankle-foot orthosis 10. Therefore, the seamless inner shell 14 preferably has no protrusions that would scratch or irritate the injured foot 100. Also, because the inner shell 14 is seamless, no pattern is required to be cut or utilized during its construction.

In some embodiments, such as that shown in FIG. 46, a wedge 38 may also be included as a further tool in addressing a condition of the injured foot 100. In the embodiment shown in FIG. 46, the wedge 38 is included within the ankle-foot orthosis 10, resting upon the inner shell 14 in the lower region of the ankle-foot orthosis 10. According to this embodiment, therefore, the wedge 38 is configured to be selectively removable and replaceable without adjustment of the ankle-foot orthosis 10. In other embodiments, the wedge 38 is formed by padding elements 26 or structural supports 24 adhered to the inner shell 14 prior to stretch molding of the outer shell 12 thereto. In such embodiments, the wedge 38 is not readily removable from the ankle-foot orthosis 10.

Figure 47:
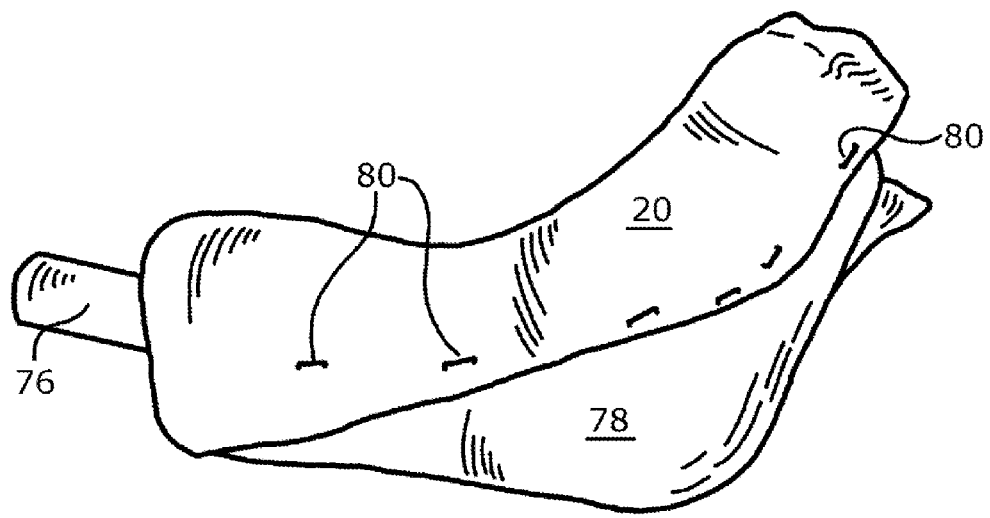
FIG. 47 is a right side perspective view after stretch molding of an interior layer of a pre-tibial shell over that shown in FIG. 34 during the construction of an ankle-foot orthosis.
Figure 48:
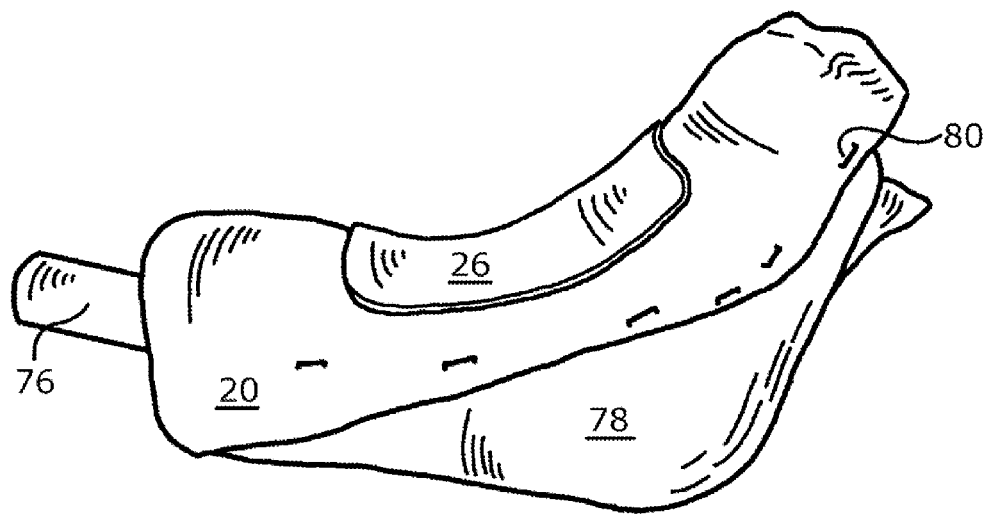
FIG. 48 is a right side perspective view following that shown in FIG. 47 after attachment of padding during the construction of an ankle-foot orthosis.

The method for constructing an ankle-foot orthosis 10 further includes the molding of a pre-tibial shell 16, which is preferably accomplished using the same lined mold of hardened hardening fluid 74 (FIG. 33) to which the inner shell 14 was stretch molded. With this mold, an interior layer 20 is stretch molded over the mold in an area corresponding to the pre-tibial area of the injured foot, as shown in FIG. 47. Preferably, the interior layer 20 is made from the same leather from which the inner shell 14 was made. It is further preferably temporarily affixed to the lined mold using temporary fasteners 80. In some embodiments, padding elements 26 are selectively adhered to selective pre-tibial padding areas. For example, according to the embodiment depicted in FIG. 48, padding elements 26 are adhered along the majority of the pre-tibial area. In other embodiments, padding elements 26 are not adhered to the interior layer 20. In still other embodiments, padding elements 26 are adhered to smaller areas. As with the padding elements 26 adhered to the inner shell 14, the number of padding elements 26 adhered, the thickness of the padding elements 26 adhered, and the selective pre-tibial padding areas to which the padding elements 26 are adhered are chosen based on the needs of the patient. Further, in some embodiments, the padding elements 26 are adhered to the selective pre-tibial padding areas via epoxy, glue, tape, or other adhesive. In other embodiments, the padding elements 26 are adhered to the selective pre-tibial padding areas via lamination, either in one layer or in multiple layers.

Figure 49:
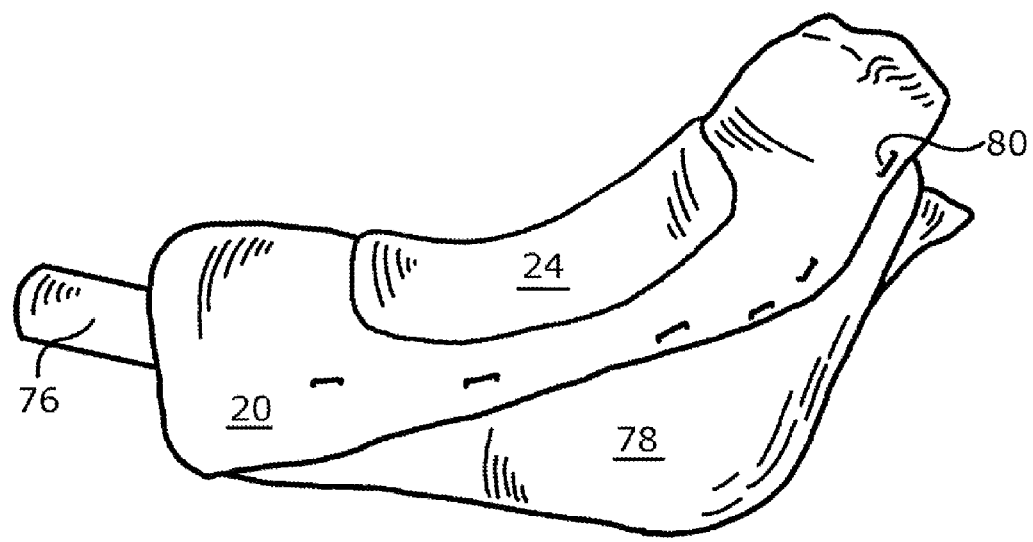
FIG. 49 is a right side perspective view following that shown in FIG. 48 after attachment of a structural support during the construction of an ankle-foot orthosis.

Further, in some embodiments, structural supports 24 are adhered to the interior layer 20 at selective pre-tibial stiffener areas. In some embodiments, the structural supports 24 are added on top of padding elements 26 already in place. However, in other embodiments, the structural supports 24 are added directly against the interior layer 20. Again, the number of structural supports 24 adhered, the thickness of the structural supports 24 adhered, the relative rigidity or flexibility of the structural supports 24 adhered, and the selective pre-tibial stiffener areas to which the structural supports 24 are adhered are chosen based on the needs of the patient. According to the embodiment depicted in FIG. 49, one structural support 24 is adhered atop the padding elements 26 (FIG. 48) along the majority of the pre-tibial area. However, in other embodiments, structural supports 24 are adhered in a smaller area or in multiple areas. Also, in some embodiments, the structural supports 24 are adhered to the selective pre-tibial stiffener areas via epoxy, glue, tape, or other adhesive. In other embodiments, the structural supports 24 are adhered to the selective pre-tibial stiffener areas via lamination, either in one layer or in multiple layers.

Figure 50:
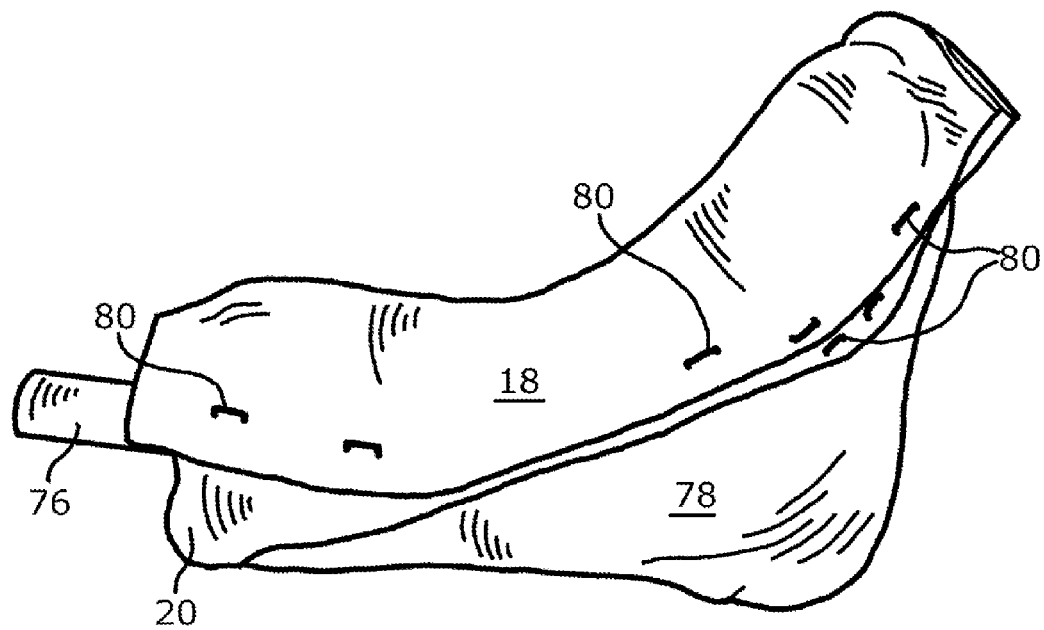
FIG. 50 is a right side perspective view following that shown in FIG. 49 after stretch molding of an exterior layer of a pre-tibial shell during the construction of an ankle-foot orthosis.
Figure 51:
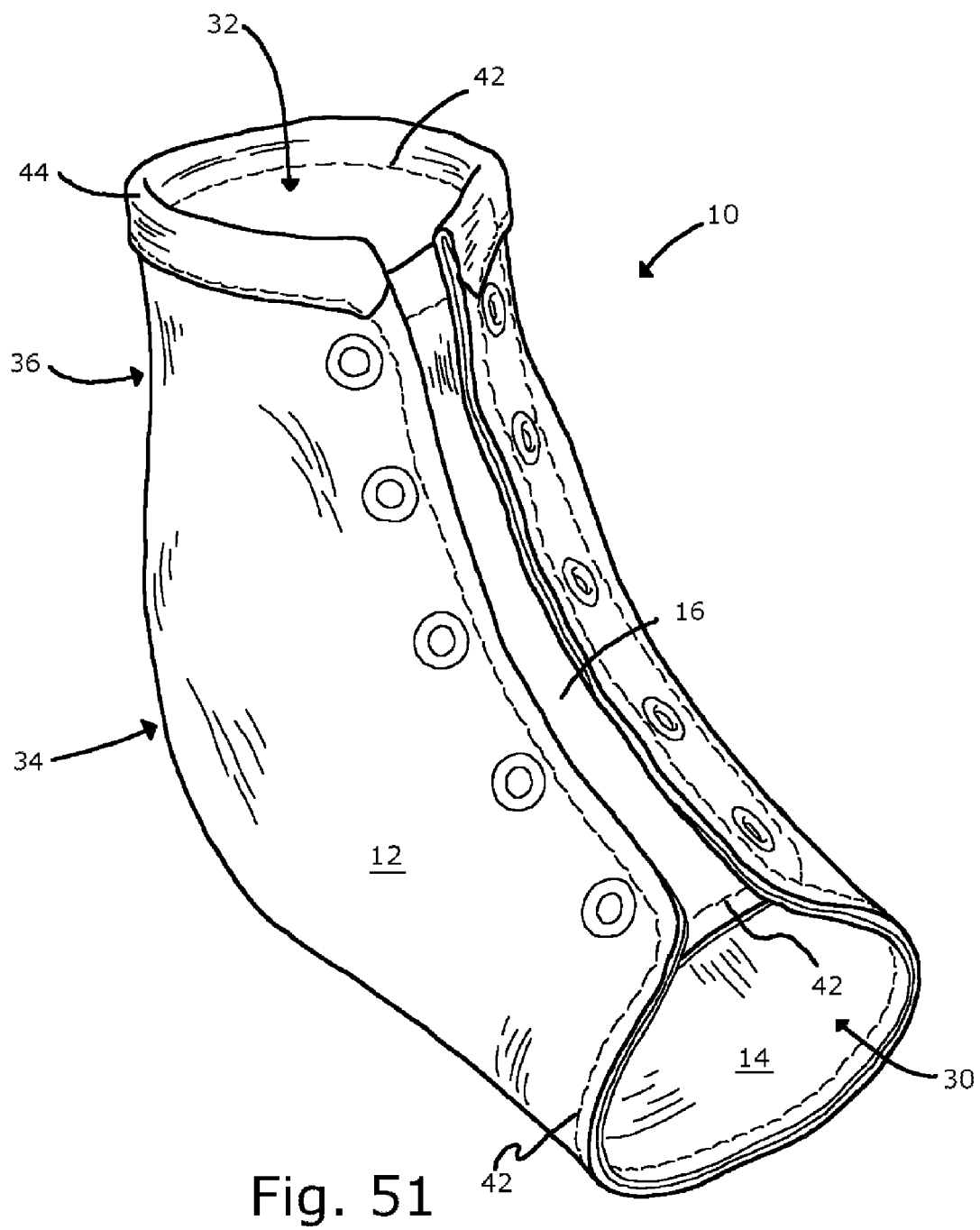
FIG. 51 is a front and right side perspective view following attachment of a pre-tibial shell to that shown in FIG. 45 during the construction of an ankle-foot orthosis.

Following inclusion of any padding elements 26 and/or structural supports 24 to the interior layer 20, an exterior layer 18 is stretch molded over the interior layer 20 and any padding elements 26 and/or structural supports 24. Preferably, the exterior layer 18 is made from the same leather from which the outer shell 12 was made. It is further preferably temporarily affixed to the interior layer 20 via temporary fasteners 80, as shown in FIG. 50. Thereafter, excess of the interior layer 20 and exterior layer 18 are trimmed and the interior layer 20 and exterior layer 18 are preferably affixed to one another via stitching 42 so as to discourage the interior layer 20 and exterior layer 18 from moving relative to one another. As shown in FIG. 51, with the pre-tibial shell 16 now formed, the pre-tibial shell 16 is attached to the boot made up of the outer shell 12 and inner shell 14 and interior layers of padding elements 26 and structural supports 24, if any.

Figure 2:
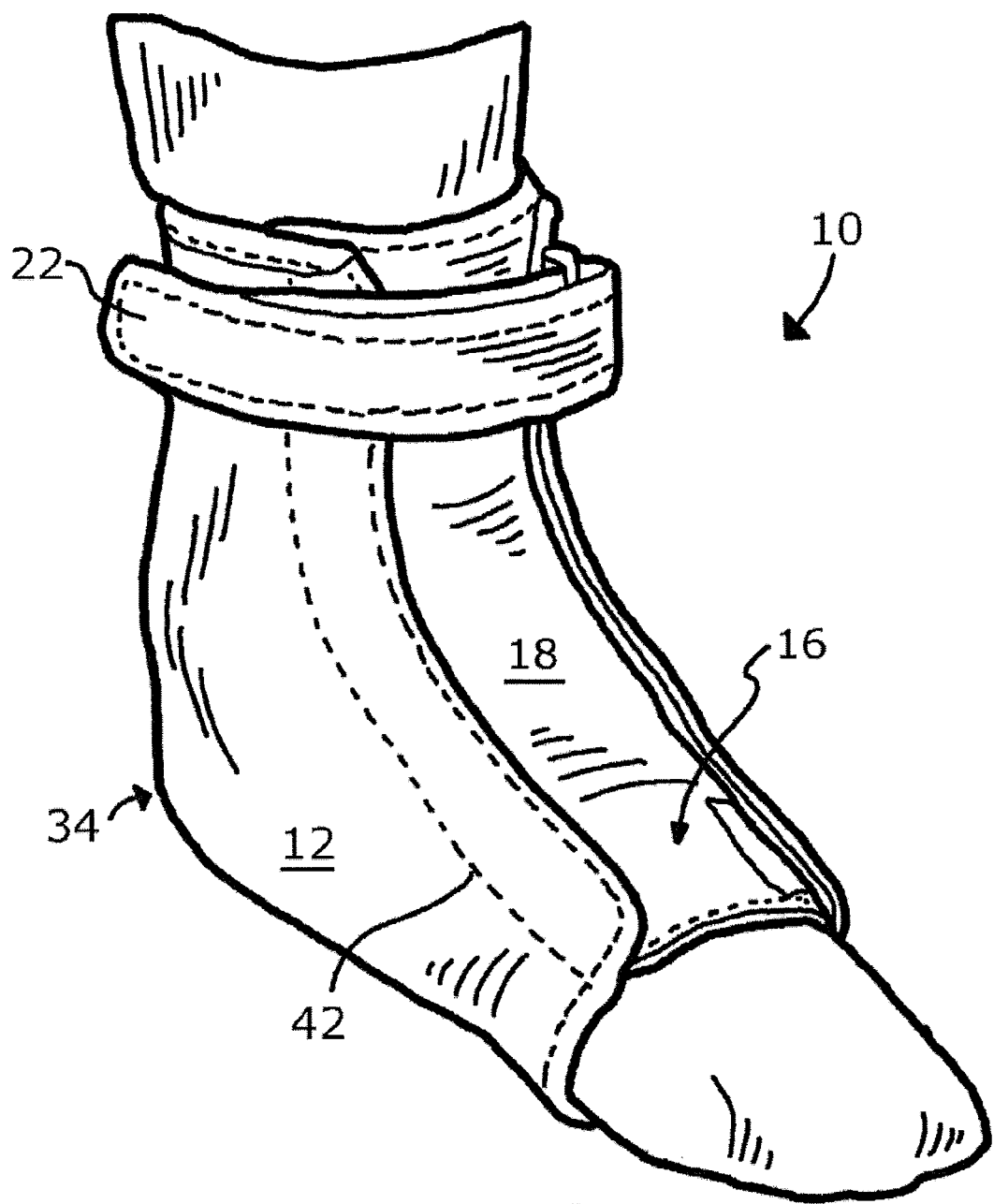
FIG. 2 is a front and right side perspective view of an ankle-foot orthosis according to a second embodiment.
Figure 3:
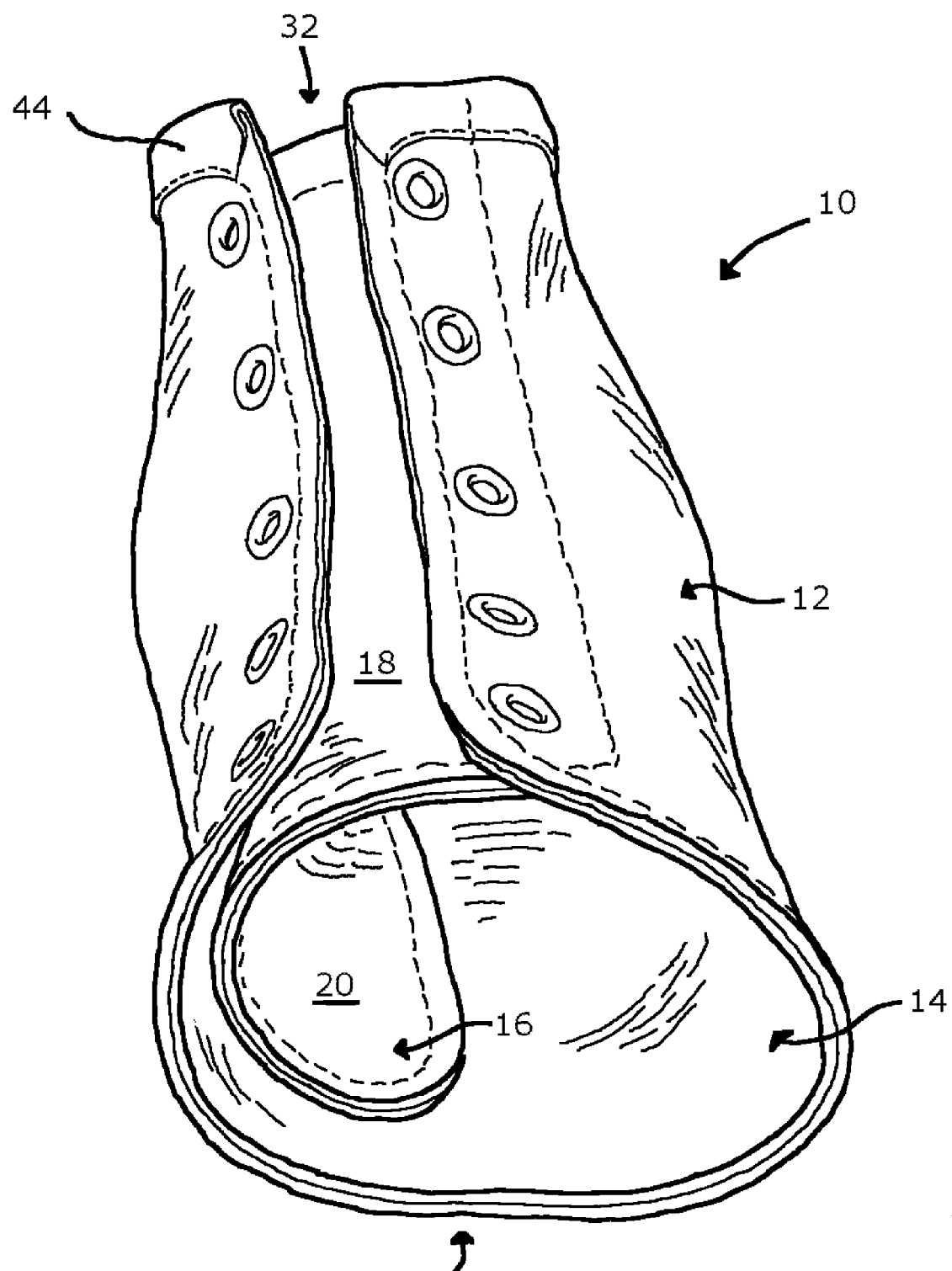
FIG. 3 is a front perspective view of an ankle-foot orthosis according to the first embodiment.
Figure 9:
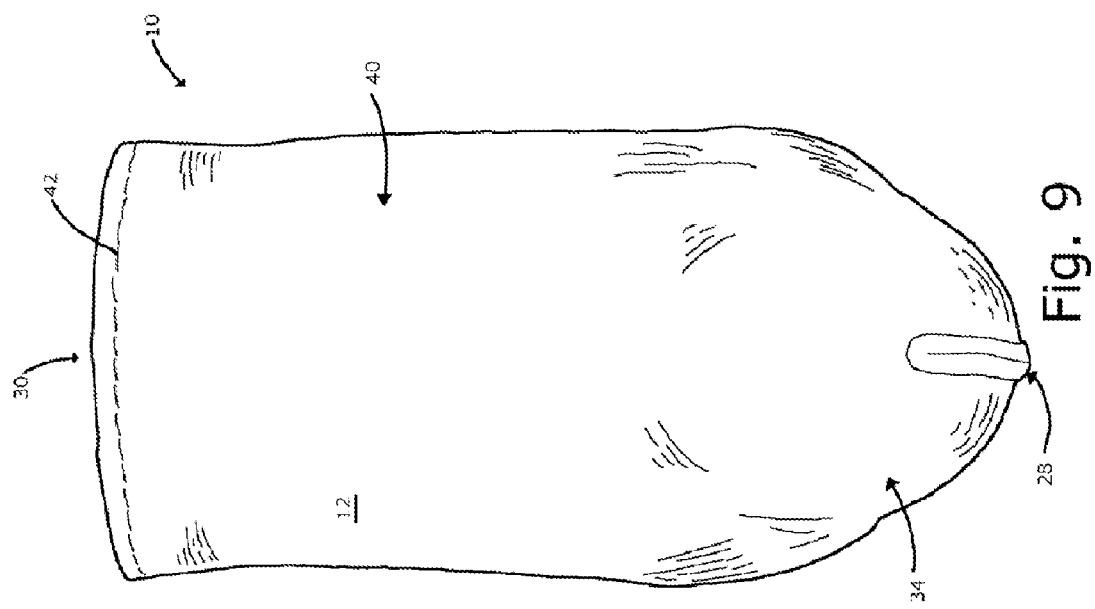
FIG. 9 is a bottom plan view of an ankle-foot orthosis according to the first embodiment.
Figure 8:
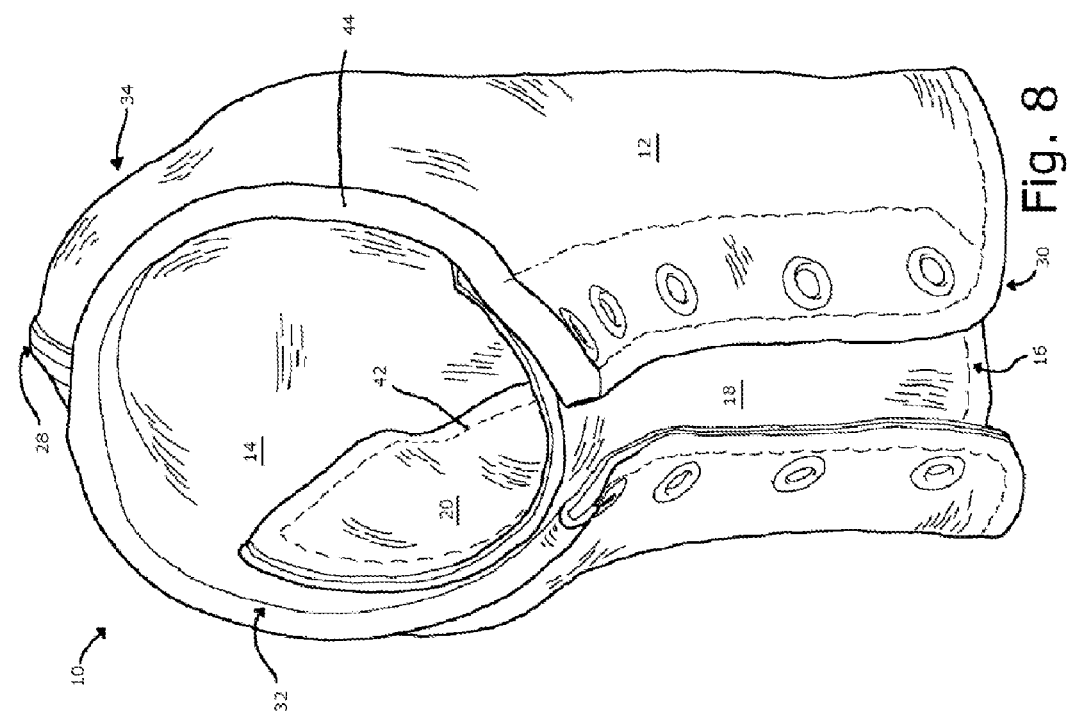
FIG. 8 is a top and front side perspective view of an ankle-foot orthosis according to the first embodiment.

The ankle-foot orthosis 10 preferably further includes a closure device 22, such as the eyelets and laces system depicted in FIG. 1 or the hook and loop attachment strap mechanism depicted in FIG. 2. In other embodiments, the closure device 22 utilizes b-rings, hooks, webbing, zippers, buttons, snaps, or combinations thereof. In some embodiments, the closure device 22 is formed or attached to the boot of the outer shell 12 and inner shell 14 prior to attachment of the pre-tibial shell 16. In other embodiments, the closure device 22 is formed or attached to the boot of the outer shell 12 and inner shell 14 after attachment of the pre-tibial shell 16.

The resulting, completed ankle-foot orthosis 10, therefore, is one custom molded to the injured foot 100 and is constructed, not to accommodate the original position of the injured foot 100, but to treat the injured foot 100 by placing it essentially into an overall corrected position. This overall corrected position in which the ankle-foot orthosis 10 is constructed has the benefit of, first, the taping of the injured foot 100 into the first corrected position wherein the second toe of the injured foot 100 is in alignment with the midline of the patient's kneecap and, in some embodiments, in which particular taping configurations have been used to address conditions of the injured foot 100, such as varus or valgus configurations, overall collapsing foot, etc. The overall corrected position in which the ankle-foot orthosis 10 is constructed has the further benefit of the corrections to position made during casting, as by dorsiflexing the injured foot 100 into the second corrected position wherein the injured foot 100 and the patient's shin form an angle in the range of seventy to one-hundred ten degrees and as by placing the injured foot 100 into the third corrected position in which the injured foot 100 is in a subtalar neutral position. The overall corrected position in which the ankle-foot orthosis 10 is constructed still further has the benefit, in some embodiments, of corrections made to the negative cast, as by cutting and realigning the negative cast. Further, in some embodiments, the overall corrected position in which the ankle-foot orthosis 10 is constructed has the benefit of corrections made to the mold, as by filing away or adding to and smoothing of areas of the mold with additional hardening fluid. Accordingly, the resulting position of the ankle-foot orthosis 10 has been corrected at several points during the construction process and does not simply accommodate an incorrectly-positioned injured foot 100.

Still further, as padding elements 26 and/or structural supports 24 have been included between the outer shell 12 and inner shell 14 and/or between the exterior layer 18 and interior layer 20 of the pre-tibial shell 16, the constructed ankle-foot orthosis 10 is further able to address particular areas of the injured foot 100 with added cushioning or structural support, as the case may be. Thus, protrusions in the injured foot 100 can be cushioned. Injured joints can be supported such that motion of the injured joint is restricted while healthy areas of the injured foot 100 are allowed to move without restriction by structural supports 24. Further, as the outer shell 12 and inner shell 14 and pre-tibial shell 16 soften through use, as the injured foot 100 becomes healthier during use of the ankle-foot orthosis 10, the increasing flexibility of the ankle-foot orthosis 10 allows for the injured foot 100 to have increasing freedom of movement. However, those areas of the ankle-foot orthosis 10 in which structural supports 24 are included do not become as increasingly flexible; thus, the most injured areas of the injured foot 100 continue to be supported and limited in movement while the remaining areas of the injured foot 100 are allowed increasing freedom of movement. Thus, the same ankle-foot orthosis 10 can be utilized as a patient's treatment progresses such that it is not necessary to first use a completely rigid cast followed by use of a separate, partially-rigid cast.

Preferably, adjustments to the relative rigidity or flexibility of the outer shell 12, inner shell 14, pre-tibial shell 16, and/or structural supports 24 may further be made after the initial construction of the ankle-foot orthosis 10. That is, following initial construction of the ankle-foot orthosis 10, the leather of the outer shell 12, inner shell 14, and/or pre-tibial shell 16 can be further subjected to stretching or softening so as to increase the relative flexibility of the outer shell 12, inner shell 14, and/or pre-tibial shell 16 in select locations. Likewise, the leather of the outer shell 12, inner shell 14, and/or pre-tibial shell 16 can be further subjected to stiffening processes so as to decrease the relative flexibility of the outer shell 12, inner shell 14, and/or pre-tibial shell 16 in select locations. As such, adjustments to the treatment of the injured foot 100 can be accomplished through post-construction changes to the ankle-foot orthosis 10 without having to recast the injured foot 100 and without having to construct a new ankle-foot orthosis 10. Thus, it is preferable for the patient having the injured foot 100 to be seen by a doctor approximately two months after initial use of the ankle-foot orthosis 10 so that any necessary adjustments can be made.

Further, in some embodiments, the outer shell 12 can be selectively removed from the inner shell 14 so as to allow access to the padding elements 26 and structural supports 24 layered therebetween. Thus, additional padding elements 26 and structural supports 24 may be included, or padding elements 26 or structural supports 24 may be removed, or the padding elements 26 and structural supports 24 already included in the ankle-foot orthosis 10 can be additionally adjusted, as with heat molding, before the inner shell 14 is again attached to the outer shell 12.

In still other embodiments, padding elements 26 and/or structural supports 24 are adhered to the outside of the outer shell 12, to provide additional padding and/or support, respectively, to the patient. Again, then, adjustments to the treatment of the injured foot 100 can be accomplished through post-construction changes to the ankle-foot orthosis 10 without having to recast the injured foot 100 and without having to construct a new ankle-foot orthosis 10. This keeps the cost of treatment low.

With regard to the treatment of the leather used for forming the inner shell 14, outer shell 12, the interior layer 20 of the pre-tibial shell 16, and the exterior layer 18 of the pre-tibial shell 16, in some embodiments, the leather is first soaked in water or alcohol to allow the leather to soften. An alcohol bath is preferably used, rather than a water bath, when it is desirable to have a resulting ankle-foot orthosis that is of high rigidity. When less initial rigidity is desired, such as for a patient that would not be harmed by some movement of the injured foot 100 during treatment, a water bath is preferably used. The leather used is also preferably not pre-stretched and is vegetable tanned, not chromium tanned. As the leather is not pre-stretched, the molding process allows for better molding to the contours of the mold made of the patient's actual foot anatomy.

In any regard, the construction of the ankle-foot orthosis is accomplished utilizing relatively-simple and inexpensive equipment, which reduces the cost of manufacturing.

While there is shown and described the present preferred embodiment of the ankle-foot orthosis and method of construction, it is to be distinctly understood that this invention is not limited thereto but may be variously embodied to practice within the scope of the following claims. From the foregoing description, it will be apparent that various changes may be made without departing from the spirit and scope of the orthoses and methods as defined by the following claims.

What is claimed is:

1. An ankle-foot orthosis for nonsurgical treatment of an injured foot of a patient, the ankle-foot orthosis comprising:
a boot comprising:
a singular inner shell comprising leather molded to a casting of the injured foot taped in a non-weight-bearing position and corrected to a position of neutral pathology; and
an outer shell substantially surrounding the singular inner shell, the outer shell comprising leather molded, at least in part, to the singular inner shell;
a pre-tibial shell comprising an interior layer and a singular exterior layer, the interior layer comprising a first leather molded to the casting, the singular exterior layer comprising a second leather different from the first leather, the singular exterior layer molded, at least in part, to the interior layer and extending a length of the boot between a top opening and a front opening of the boot, the pre-tibial shell configured to at least partially rigidly conform to a pre-tibial region of the injured foot; and
at least one structural support disposed between the singular inner shell and the outer shell, the at least one structural support configured to rigidly support an injured area of the injured foot;
the singular inner shell, the outer shell, and the pre-tibial shell configured to at least partially flex during movement of the injured foot and to increase in flexibility with use except where the at least one structural support is disposed between the singular inner shell and the outer shell;
the ankle-foot orthosis being, at first use, an essentially rigid cast providing circumferential control to the injured foot; and
the ankle-foot orthosis accommodating tri-planar flexing.

2. The ankle-foot orthosis of claim 1, wherein the singular inner shell does not comprise a seam.

3. The ankle-foot orthosis of claim 1, further comprising a closure device configured to selectively reduce a width of a pre-tibial slit defined by edges of the singular inner shell and the outer shell proximate to the pre-tibial shell.

4. The ankle-foot orthosis of claim 1, further comprising at least one padding element disposed between the singular inner shell and the outer shell, the at least one padding element positioned to provide cushioning to an area of the injured foot.

5. The ankle-foot orthosis of claim 1, further comprising a top cuff comprising a top portion of the singular inner shell overlapping an exterior region of a top portion of the outer shell, the top cuff defining the top opening.

6. The ankle-foot orthosis of claim 1, wherein the ankle-foot orthosis has a total weight of fewer than 170 grams, the ankle-foot orthosis configured for use by a patient having a weight of 160 pounds.

7. The ankle-foot orthosis of claim 1, wherein the singular inner shell comprises vegetable-tanned leather not pre-stretched before molding, not chemically dyed, and of a weight between 1 ounce per square foot and 3 ounces per square foot.

8. The ankle-foot orthosis of claim 1, wherein the outer shell comprises vegetable-tanned leather not pre-stretched, not chemically dyed, and of a weight between 3 ounces per square foot and 6 ounces per square foot.

9. A method for constructing an ankle-foot orthosis for use in treating a patient having an injured foot, the method comprising:
applying tape to the injured foot to encourage the injured foot into a first corrected position wherein the second toe of the injured foot is in alignment with the midline of the patient's kneecap;
wrapping the injured foot with casting material to surround a majority of the injured foot without surrounding the patient's toes or upper calf, the patient's weight not bearing upon the injured foot during wrapping;
dorsiflexing the injured foot into a second corrected position wherein the injured foot and the patient's shin define an angle in the range of from seventy degrees to one-hundred ten degrees;
placing the injured foot into a third corrected position wherein the injured foot is in a subtalar neutral position;
forming the casting material into a negative cast of the injured foot in at least the third corrected position;
forming a mold from the negative cast;
molding a boot, comprising:
stretch molding a seamless inner leather shell over the mold;
selectively adhering structural supports to the seamless inner leather shell in selective stiffener areas;
stretch molding an outer leather shell over the seamless inner leather shell and the structural supports; and
removing the boot from the mold;
molding a pre-tibial shell configured to at least partially rigidly conform to a pre-tibial region of the injured foot, comprising:
stretch molding a first piece of leather material over the mold in an area corresponding to the pre-tibial region of the injured foot to form an interior layer;
stretch molding a second piece of leather material over the interior layer to form a singular exterior layer extending a length of the boot between a top opening and a front opening of the boot, the second piece of leather material being different from the first piece of leather material; and
removing the pre-tibial shell from the mold; and
attaching the pre-tibial shell to the boot to form an ankle-foot orthosis configured to at least partially flex during movement of the injured foot and to increase in flexibility with use except where the structural supports are disposed between the seamless inner leather shell and the outer leather shell, the ankle-foot orthosis being, at initial construction, an essentially rigid cast configured to provide circumferential control to the injured foot; and the ankle-foot orthosis accommodating tri-planar flexing.

10. The method of claim 9, further comprising, prior to wrapping the injured foot with the casting material:
inserting the injured foot into a stockinet sock while the patient's weight is not bearing upon the injured foot; and
placing an aluminum splint along a front portion of the injured foot extending from an area proximate to the patient's toes to an area proximate to the patient's shin, the front portion being proximate to the injured foot's pre-tibial region.

11. The method of claim 9, wherein molding a pre-tibial shell further comprises selectively adhering pre-tibial padding to the interior layer at selective pre-tibial padding areas.

12. The method of claim 9, wherein molding a pre-tibial shell further comprises selectively adhering pre-tibial structural supports to the interior layer at selective pre-tibial stiffener areas.

13. The method of claim 9, wherein wrapping the injured foot with casting material comprises wrapping the injured foot with a fiberglass casting material.

14. The method of claim 9, wherein forming a mold from the negative cast comprises:
removing the negative cast from the injured foot;
inserting a rod at least partially into the negative cast;

pouring a hardening fluid into the negative cast; and
allowing the hardening fluid to harden.

15. The method of claim 9, wherein molding a boot further comprises:
   selectively adhering padding to the seamless inner leather shell in selective padding areas; and
   wherein stretch molding the outer leather shell comprises stretch molding the outer leather shell over the seamless inner leather shell, the padding, and the structural supports.

16. The method of claim 9, wherein molding a boot further comprises selectively stiffening the outer leather shell.

17. The method of claim 9, further comprising attaching a closure device to the boot.

18. The method of claim 9, wherein:
forming a mold from the negative cast comprises:
   separating the negative cast into an upper negative cast portion and a lower negative cast portion; and
   aligning the upper negative cast portion relative to the lower negative cast portion into a fourth corrected position; and
forming the casting material into a negative cast of the injured foot in at least the third corrected position comprises forming the casting material into a negative cast of the injured foot in the fourth corrected position.

19. An ankle-foot orthosis comprising:
   an inner shell comprising leather substantially conforming to a non-weight-bearing foot taped and positioned to a neutral pathology;
   at least one of a structural support and a padding element disposed over the inner shell;
   an outer shell comprising another leather substantially conforming to the inner shell and the at least one of the structural support and the padding element, the another leather having a weight (ounces/ft$^2$) greater than a weight (ounces/ft$^2$) of the leather of the inner shell; and
   a pre-tibial shell comprising:
      an interior layer comprising the leather substantially conforming to a pre-tibial area of the non-weight-bearing foot taped and positioned to the neutral pathology; and
      an exterior layer comprising the another leather substantially conforming to the interior layer and having an edge aligning with an edge of the interior layer along at least one of a top opening and a front opening of the ankle-foot orthosis;
   the inner shell, the outer shell, and the pre-tibial shell configured to at least partially increase in flexibility with wear of the ankle-foot orthosis; and
   the ankle-foot orthosis accommodating tri-planar flexing of an injured foot wearing the ankle-foot orthosis.

20. The ankle-foot orthosis of claim 19, wherein the pre-tibial shell further comprises, disposed between the interior layer and the exterior layer, at least one of pre-tibial structural supports and pre-tibial padding.

* * * * *

UNITED STATES PATENT AND TRADEMARK OFFICE
CERTIFICATE OF CORRECTION

| | | |
|---|---|---|
| PATENT NO. | : 8,512,269 B1 | Page 1 of 1 |
| APPLICATION NO. | : 12/720544 | |
| DATED | : August 20, 2013 | |
| INVENTOR(S) | : William Scott Stano and Scott David Pixley | |

It is certified that error appears in the above-identified patent and that said Letters Patent is hereby corrected as shown below:

In the specification:

COLUMN 7, LINE 37, change "is left side a left side" to --is a left side--
COLUMN 10, LINE 27, change "inner 14" to --inner shell 14--

Signed and Sealed this
Twenty-third Day of February, 2016

Michelle K. Lee
*Director of the United States Patent and Trademark Office*